(12) United States Patent
Xie et al.

(10) Patent No.: US 11,530,436 B2
(45) Date of Patent: Dec. 20, 2022

(54) MULTIPLEX END-TAGGING AMPLIFICATION OF NUCLEIC ACIDS

(71) Applicant: President and Fellows of Harvard College, Cambridge, MA (US)

(72) Inventors: Xiaoliang Sunney Xie, Lexington, MA (US); Dong Xing, Cambridge, MA (US); Chi-Han Chang, Cambridge, MA (US); Longzhi Tan, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 209 days.

(21) Appl. No.: 16/615,872

(22) PCT Filed: May 23, 2018

(86) PCT No.: PCT/US2018/034162
§ 371 (c)(1),
(2) Date: Nov. 22, 2019

(87) PCT Pub. No.: WO2018/217912
PCT Pub. Date: Nov. 29, 2018

(65) Prior Publication Data
US 2020/0102598 A1    Apr. 2, 2020

Related U.S. Application Data

(60) Provisional application No. 62/509,981, filed on May 23, 2017.

(51) Int. Cl.
*C12Q 1/6806*    (2018.01)
*C12Q 1/6844*    (2018.01)
*C12Q 1/6874*    (2018.01)

(52) U.S. Cl.
CPC ......... *C12Q 1/6806* (2013.01); *C12Q 1/6844* (2013.01); *C12Q 1/6874* (2013.01); *C12Q 2521/101* (2013.01); *C12Q 2521/507* (2013.01); *C12Q 2525/155* (2013.01); *C12Q 2535/122* (2013.01)

(58) Field of Classification Search
CPC .. C12Q 1/6806; C12Q 1/6844; C12Q 1/6874; C12Q 2521/101; C12Q 2521/507; C12Q 2525/155; C12Q 2535/122; C12N 15/108
See application file for complete search history.

(56) References Cited

U.S. PATENT DOCUMENTS

| | | |
|---|---|---|
| 2013/0017978 A1 | 1/2013 | Kavanagh et al. |
| 2014/0045728 A1* | 2/2014 | Church ............... C12Q 1/6834 506/26 |
| 2014/0162897 A1 | 6/2014 | Grunenwald et al. |
| 2015/0337298 A1* | 11/2015 | Xi ....................... C12Q 1/6806 506/26 |
| 2016/0369266 A1 | 12/2016 | Belyaev et al. |
| 2019/0203204 A1* | 7/2019 | Xie ........................ C40B 50/18 |

FOREIGN PATENT DOCUMENTS

| | | |
|---|---|---|
| WO | 2014/142850 A1 | 9/2014 |
| WO | 2016/130704 A2 | 8/2016 |
| WO | 2017/015075 A1 | 1/2017 |
| WO | WO 2017015075 * | 1/2017 |
| WO | 2018/031631 A1 | 2/2018 |
| WO | 2018/039969 A1 | 3/2018 |

OTHER PUBLICATIONS

Buenrostro et al. "Single-cell chromatin accessibility reveals principles of regulatory variation," Nature, Jun. 17, 2015 (Jun. 15, 2015), vol. 523, pp. 486-490. entire document.
Buenrostro et al. "Transposition of Native Chromatin for Fast and Sensitive Epigenomic Profiling of Open Chromatin, DNA-Binding Proteins and Nucleosome position," Nature Methods, Oct. 6, 2013 (Oct. 6, 2013), vol. 10, Iss. 12, pp. 1213-1218. entire document.
Chen et al. "ATAC—See Reveals the Accessible Genome by Transposase Mediated Imaging and Sequencing," Nature Methods, Oct. 17, 2016 (Oct. 17, 2016), vol. 13, Iss. 12, pp. 1013-1020. entire document.
Chen et al. "Single-Cell Whole Genome Analyses by Linear Amplification via Transposon Insertion (LIANTI)," Science, Apr. 14, 2017 (Apr. 14, 2017), vol. 356, pp. 189-194. entire document.
International Search Report and Written Opinion based on PCT/US2018/034162 dated Aug. 8, 2018.

* cited by examiner

*Primary Examiner* — Cynthia B Wilder
(74) *Attorney, Agent, or Firm* — Banner & Witcoff, Ltd.

(57) ABSTRACT

The present disclosure provides a method for assembly of genomic DNA using multiplex end-tagging amplification of genomic fragments.

24 Claims, 8 Drawing Sheets
Specification includes a Sequence Listing.

T: Transposase binding site

M: Multiplex priming site

Multiplex PCR amplification

MULTIPLEX END-TAGGING AMPLIFICATION OF NUCLEIC ACIDS

RELATED APPLICATIONS

This application is a National Stage Application under 35 U.S.C. 371 of co-pending PCT application PCT/US18/34162 designating the United States and filed May 23, 2018; which claims the benefit of U.S. provisional application No. 62/509,981 filed on May 23, 2017 each of which are hereby incorporated by reference in their entireties.

STATEMENT OF GOVERNMENT INTERESTS

This invention was made with government support under CA 186693 from the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on May 23, 2018, is named 010498_01103_WO_SL.txt and is 4.971 bytes in size.

BACKGROUND

Field of the Invention

Embodiments of the present invention relate in general to methods and compositions for single cell genome sequencing, such as DNA from a single cell.

Description of Related Art

The capability to perform single-cell genome sequencing is important in studies where cell-to-cell variation and population heterogeneity play a key role, such as tumor growth, stem cell reprogramming, embryonic development, etc. Single cell genome sequencing is also important when the cell samples subject to sequencing are precious or rare or in minute amounts. Important to accurate single-cell genome sequencing is the initial amplification of the genomic DNA which can be in minute amounts.

Multiple displacement amplification (MDA) is a common method used in the art with genomic DNA from a single cell prior to sequencing and other analysis. In this method, random primer annealing is followed by extension taking advantage of a DNA polymerase with a strong strand-displacement activity. The original genomic DNA from a single cell is amplified exponentially in a cascade-like manner to form hyperbranched DNA structures. Another method of amplifying genomic DNA from a single cell is described in Zong, C., Lu, S., Chapman, A. R., and Xie, X. S. (2012), Genome-wide detection of single-nucleotide and copy-number variations of a single human cell, Science 338, 1622-1626 which describes Multiple Annealing and Looping-Based Amplification Cycles (MALBAC). Another method known in the art is degenerate oligonucleotide primed PCR or DOP-PCR. Several other methods used with single cell genomic DNA include Cheung, V. G. and S. F. Nelson, Whole genome amplification using a degenerate oligonucleotide primer allows hundreds of genotypes to be performed on less than one nanogram of genomic DNA. Proceedings of the National Academy of Sciences of the United States of America. 1996, 93(25): p. 14676-9; Telenius, H., et al., Degenerate oligonucleotide-primed PCR: general amplification of target DNA by a single degenerate primer, Genomics, 1992, 13(3): p. 718-25; Zhang, L., et al., Whole genome amplification from a single cell: implications for genetic analysis. Proceedings of the National Academy of Sciences of the United States of America, 1992, 89(13): p. 5847-51; Lao. K., N. L. Xu. and N. A. Straus, Whole genome amplification using single-primer PCR, Biotechnology Journal, 2008, 3(3): p. 378-82; Dean, F. B., et al., Comprehensive human genome amplification using multiple displacement amplification, Proceedings of the National Academy of Sciences of the United States of America, 2002, 99(8): p. 5261-6; Lage. J. M., et al., Whole genome analysis of genetic alterations in small DNA samples using hyperbranched strand displacement amplification and array-CGH. Genome Research, 2003, 13(2): p. 294-307; Spits, C., et al., Optimization and evaluation of single-cell whole-genome multiple displacement amplification, Human Mutation, 2006, 27(5): p. 496-503; Gole, J., et al., Massively parallel polymerase cloning and genome sequencing of single cells using nanoliter microwells, Nature Biotechnology, 2013. 31(12): p. 1126-32; Jiang. Z., et al., Genome amplification of single sperm using multiple displacement amplification, Nucleic Acids Research, 2005, 33(10): p. e91; Wang, J., et al., Genome-wide Single-Cell Analysis of Recombination Activity and De Novo Mutation Rates in Human Sperm, Cell, 2012, 150(2): p. 402-12; Ni, X., Reproducible copy number variation patterns among single circulating tumor cells of lung cancer patients, PNAS, 2013, 110, 21082-21088; Navin, N., Tumor evolution inferred by single cell sequencing, Nature, 2011, 472 (7341):90-94; Evrony, G. D., et al., Single-neuron sequencing analysis of 11 retrotransposition and somatic mutation in the human brain. Cell, 2012, 151(3): p. 483-96; and McLean, J. S., et al., Genome of the pathogen Porphyromonas gingivalis recovered from a biofilm in a hospital sink using a high-throughput single-cell genomics platform. Genome Research, 2013, 23(5): p. 867-77. Methods directed to aspects of whole genome amplification are reported in WO 2012/166425. U.S. Pat. No. 7,718,403. US 2003/0108870 and U.S. Pat. No. 7,402,386.

In vitro transposition has been used in certain applications of DNA amplification. In such methods, target DNA is simultaneously fragmented and tagged producing fragments tagged with desired DNA sequences for downstream processing. As a library preparation method, in vitro transposition has been utilized in the Nextera technology of Illumina. Inc, to simultaneously fragment DNA and tag each fragment with appropriate sequences for next-generation sequencing (US20110287435). As a tool for studying single-cell genomes and epigenomes, in vitro transposition has been used by Buenrostro et al. to profile chromatin accessibility (Buenrostro, J. D., Wu. B., Litzenburger, U. M., Ruff, D., Gonzales. M. L., Snyder, M. P., . . . & Greenleaf, W. J. (2015). Single-cell chromatin accessibility reveals principles of regulatory variation. Nature, 523(7561), 486-490), by Ramani et al. to study three-dimensional chromosome conformation (Ramani, V., Deng, X., Qiu, R., Gunderson, K. L., Steemers, F. J., Disteche, C. M., . . . & Shendure, J. (2017). Massively multiplex single-cell Hi-C. Nature Methods, 14(3), 263-266), and by Zahn et al. to amplify single-cell genomes directly into sequencing library (Zahn, H., Steif, A., Laks, E., Eirew, P., VanInsberghe, M., Shah. S. P., . . . & Hansen. C. L. (2017). Scalable whole-genome single-cell library preparation without preamplification. Nature Methods, 2017). However, all these methods suffer from approximately 50% loss of the original target nucleic acid. This happens because two transposon sequences are used for tagging, hereafter denoted as A and B: After transposons A and B are tagged to the target DNA, four different types of DNA fragments can be generated, which are fragments tagged with A-A, B-B, A-B or B-A at the two ends of each fragment. Only fragments tagged with A-B or B-A, which account for 50% of the total transposition products, are suitable for PCR amplification or paired-end sequencing. The other 50% of the fragments, which are tagged with A-A or B-B, will be lost. Such a loss rate is certainly undesirable, and potentially unacceptable, for samples with a limited amount of DNA, including rare, unique or valuable single-cell samples, such as a single cell to be used for preimplantation genetic screening. An additional transposition method is described in WO2016/073690, however such method does not reduce the 50% loss resulting from transposition bias.

Accordingly, a need exists for further methods of amplifying small amounts of genomic DNA, such as from a single cell or a small group of cells where amplification loss is reduced.

SUMMARY

The present disclosure provides a method for genomic DNA fragmentation using a plurality of transposomes where each member of the plurality of transposomes includes two transposon nucleic acid sequences having priming site sequences. According to one aspect, the priming site sequence of each transposon nucleic acid sequence of the transposome is the same. According to one aspect, the priming site sequence of each transposon nucleic acid sequence of the transposome is different. According to one aspect, each member of the plurality of transposomes may include a unique and/or different priming site sequence. According to one aspect, each member of the plurality of transposomes may include two unique and/or different priming site sequences, one for each transposon in the transposome. In this manner, a set of transposomes are provided having a unique primer binding site sequence (or two unique and/or different priming site sequences) associated therewith and which can be used to distinguish transposomes. Stated, differently, the primer binding site sequences of the transposons within the transposome may be the same or may be different or nonidentical. The primer binding site sequences of the transposomes in two adjacent transposomes attached to a target nucleic acid sequence and used to make a fragment are nonidentical, such as with a high probability. The transposons may be referred to as multiplex transposons to the extent that each transposon within a transposome has a different priming site sequence. The priming sites within a library of transposomes may be referred to as multiplex priming sites to the extent that each transposome has a priming site that is different or nonidentical or unique from other priming sites within other transposomes within the set of transposomes. According to one aspect, the method provides the step of binding transposomes from a library or plurality of transposomes along a target nucleic acid sequence such that adjacent transposomes have different primer binding site sequences. In this manner, the ends of the fragmentation site will be tagged with different primer binding site sequences. This can be accomplished whether a transposome has the same primer binding site sequence for each of its two transposon DNA or whether a transposome has different primer binding site sequence for each of its two transposon DNA. In this manner, the multiplex end-tagging amplification method described herein uses multiple priming sequences to create target DNA fragments tagged by different sequences at the two ends. The multiplex end-tagging amplification method can be carried out whether the two transposon sequences within a transposome are the same or are different, as long as two adjacent transposome, i.e., directly adjacent so as to form a fragment sequence, carry different transposon primer binding site sequences where the fragment has different primer binding site sequences at each end.

According to one aspect, the use of multiplex priming site sequences within a set of transposomes reduced loss rate when a transposition method is used to fragment and tag a genomic nucleic acid sequence, such as a genomic nucleic acid sequence of a single cell. According to the teachings herein, when there are N different transposon sequences in the reaction mixture, i.e. when the number of unique priming site sequences is N, the chance of a DNA fragment tagged by the same transposon sequence, namely the loss rate, is 1/N. The present disclosure, therefore, provides a method for altering the number of unique priming site sequences, i.e. the number N, to control the loss rate. For example, when there are 20 different transposon sequences, for use with DNA obtained from a human single cell, the loss rate is $\frac{1}{20}$ or 5%.

The method described herein creating a plurality of fragments uses a set of transposomes where each member of the set of transposomes has one or two different primer binding site sequences and where each member of the set of transposomes has one or two unique or different priming binding sites compared to each other member of the set of transposomes, such as with a high probability. In this manner, adjoining ends of fragments are barcoded with different and/or unique end barcode sequences during the fragmentation process to create fragments having unique barcode sequences (priming site sequences) on each end. In this manner, opposite ends of fragments are barcoded with different and/or unique end barcode sequences with a high probability during the fragmentation process to create fragments having different barcode sequences (priming site sequences) on each end. In this manner, the two opposite ends of fragments are barcoded with different and/or unique end barcode sequences during the fragmentation process to create fragments having unique barcode sequences (priming site sequences) on each end. According to one aspect, a transposome library is used to make fragments of genomic DNA in aqueous media where a unique barcode sequence is inserted or attached to each end of the genomic DNA at a site which has been cut by the transposase of the transposome. Since each transposome has one or two different and/or unique priming site sequences compared to other transposome members of the set or plurality or library, each fragment will have unique priming site sequences (bartcode sequences) on each end. The present disclosure contemplates fragmenting genomic DNA into a plurality of fragments, such as 5 or more fragments, 10 or more fragments, 100 or more fragments, 1000 or more fragments, 10,000 or more fragments, 100,000 or more fragments, 1,000,000 or more fragments, or 10,000,000 or more fragments using a transposome library as described herein. According to one aspect depending on the number of unique and/or different primer binding site sequences, a transposome library includes 5 to 10 types or kinds of transposome members, 10 to 100 types or kinds of transposome members, 100 or more types or kinds of transposome members, 1000 or more types or kinds of transposome members, 10,000 or more types or kinds of transposome members, 100,000 or more types or kinds of transposome members, 1,000,000 or more types or kinds of transposome members, or 10,000,000 or more types or kinds of transposome members or between 5 and 50 types or kinds of transposome members.

According to one aspect, each transposome includes two transposases and two transposon DNA. Each of the two transposon DNA of the transposome includes a transposase binding site and a primer binding site sequence. According to one aspect, the transposon DNA includes a single transposase binding site and a unique primer binding site sequence. Each transposon DNA is a separate nucleic acid bound to a transposase at the transposase binding site. The transposome is a dimer of two separate transposases each bound to its own transposon DNA. The dimer may have the same primer binding site sequences on each transposon or may have different primer binding site sequences on each transposon. According to one aspect, the transposome includes two separate and individual transposon DNA, each bound to its own corresponding transposase. According to one aspect, the transposome includes only two transposases and only two transposon DNA. According to one aspect, the two transposon DNA as part of the transposome are separate, individual or non-linked transposon DNA, each bound to its own corresponding transposase.

According to one aspect, each transposome member of the library includes a unique and different priming site sequence. The same unique and different priming site sequence may be present on each transposon DNA of the transposome or a different unique and different priming site sequence may be present on each transposon DNA of the transposome. In this manner, each transposome includes a unique and different priming site sequence that is unique and different from the priming site sequences of any other transposome in the transposome library. According to one aspect, the transposome library may include transposome members that have the same priming site sequences as other transposome members, although the probability is relatively small or insignificant. In this manner, the transposome library may be considered to be a subset of the prepared collection of transposomes, where the subset includes only transposomes with a unique and different priming site sequence, as the objective is to fragment genomic DNA where each fragment cut site has different priming site sequences. It is to be understood that the objective of fragmenting genomic DNA where each fragment cut site has a different priming site sequence may be accomplished where adjacent transposomes each have a unique and different priming site sequence, though it may be shared by the two transposons of the transposome. It is to be understood that the objective of fragmenting genomic DNA where each fragment cut site has a different priming site sequence may be accomplished where adjacent transposomes each have two unique and different priming site sequences, where each transposon of the transposome has a unique and different priming site sequences.

It is to be understood that an insignificant number of cut sites may share the same priming site sequence due to transposome library preparation. For example, for a given library preparation method, it is mathematically possible that multiple molecules of transposome with the same priming site sequence exist, but the library is prepared such that the number of different priming site sequences significantly exceeds the number of transposome molecules that will actually be inserted into the target genome. According to one aspect, the transposome library may include transposome members that have the same two priming site sequences, i.e., the priming site sequences are identical or the same, although this priming site sequence is unique compared to any other transposon DNA of tranposome members of the transposome library. To make such a transposome library, each transposome member is made separately by mixing transposase and the transposon DNA which contain the unique priming site sequence. All the transpome members are then be mixed together to form the transposome library.

According to one aspect, a transposome library is prepared by mixing all transposon sequences together with transposase to form transposome. In this method, most transposomes have different transposon sequences, but the chance of a transposome carrying the same transposon sequences is 1/N. According to another method of making a transposome library, each type of transposon sequence is mixed with transposase separately, and then all the tranposome are mixed to form the transposome library. In this method, all the tranposomes will have same transposon sequences.

According to one aspect, the number of unique and/or different priming site sequences is between 5 and 50, 10 and 50, 15 and 45, 20 and 40 or between 1 and 1,000, 1 and 10,000, 1 and 100,000, 1 and 1,000,000 or 1 and 10,000,000. According to one aspect, the number of cut sites in the genomic DNA is determined or tuned by the concentration of transposomes, with the higher concentration resulting in a higher number of cut sites and a lower concentration resulting in a lower number of cut sites. According to one aspect, the number of transposomes and associated different and/or unique priming site sequences is selected such that substantially all of the cut sites have two different and/or unique priming site sequences. According to one aspect, more than 90% of the cut sites have two different and/or unique priming site sequences, more than 95% of the cut sites have two different and/or unique priming site sequences, 96% of the cut sites have two different and/or unique priming site sequences, 97% of the cut sites have two different and/or unique priming site sequences, 98% of the cut sites have two different an/or unique priming site sequences, 99% of the cut sites have two different and/or unique priming site sequences, 99.5% of the cut sites have two different and/or unique priming site sequences, or 100% of the cut sites have two different and/or unique priming site sequences.

The transposome library is then used to cut the genomic DNA and each transposome inserts or attaches its priming site sequences in each of the transposon DNA at the ends of the cut site. Where adjacent transposomes have unique and different priming site sequences compared to each other, the cut site will have a unique and different priming site sequence at each end of the site, i.e. the priming site sequences inserted will be different. In this manner, a plurality or most or substantially all fragments produced by the transposome library have a different and/or unique priming site sequence on each end, i.e. opposite ends, of the fragment, insofar as adjacent transposomes have unique and different priming site sequences compared to each other. The transposase can then be removed from each fragment followed by a gap fill-in step, by for example, a polymerase extension step. The resulting double stranded nucleic acid fragment sequence can then be amplified, for example using multiplex PCR amplification. The fragments can then be sequenced and the sequence of the genomic DNA can be determined.

According to one aspect, the transposon DNA of the transposome can include sequences facilitating amplification methods, such as specific primer sequences or transcription promoter sequences which can be attached to the fragments so that the fragments can be amplified prior to sequencing, such as by PCR or RNA transcription using methods known to those of skill in the art. It is to be understood that the present disclosure contemplates different amplification methods for amplifying the fragments and different sequencing methods for sequencing the amplicons are not limited to any particular amplification or sequencing method.

Embodiments of the present disclosure are directed to a method of multiplex end-tagging amplification of nucleic acids, such as genomic DNA, such as a small amount of genomic DNA or a limited amount of DNA such as a genomic sequence or genomic sequences obtained from a single cell or a plurality of cells of the same cell type or from a tissue, fluid or blood sample obtained from an individual or a substrate. According to certain aspects of the present disclosure, the methods described herein can be performed in a single tube with a single reaction mixture. According to certain aspects of the present disclosure, the nucleic acid sample can be within an unpurified or unprocessed lysate from a single cell. Nucleic acids to be subjected to the methods disclosed herein need not be purified, such as by column purification, prior to being contacted with the various reagents and under the various conditions as described herein. The methods described herein reduce the loss rate, i.e., loss of the original target nucleic acid so as to assist in providing substantial and uniform coverage of the entire genome of a single cell producing amplified DNA for high-throughput sequencing.

Embodiments of the present invention relate in general to methods and compositions for making DNA fragments, for example, DNA fragments from the whole genome of a single cell which may then be subjected to amplification and sequencing methods known to those of skill in the art and as described herein. According to certain aspects, methods of making nucleic acid fragments described herein utilize a transposome library. According to one aspect, a transposase as part of a transposome is used to create a set of double stranded genomic DNA fragments. According to certain aspects, the transposases have the capability to bind to transposon DNA and dimerize when contacted together, such as when being placed within a reaction vessel or reaction volume, forming a transposase/transposon DNA complex dimer called a transposome. Each transposon DNA of the transposome includes a double stranded transposase binding site and a first nucleic acid sequence including a priming site sequence and optionally functional sequences such as a transcription promoter site. The first nucleic acid sequence may be in the form of a single stranded extension. Each transposome of the transposome library includes a unique and different priming site sequence that are different from the priming site sequences of each remaining member of the transposome library. According to one aspect, each transposome of the transposome library includes two unique and different priming site sequence that are different from the priming site sequences of each remaining member of the transposome library.

The transposomes have the capability to randomly bind to target locations along double stranded nucleic acids, such as double stranded genomic DNA, forming a complex including the transposome and the double stranded genomic DNA. The transposases in the transposome cleave the double stranded genomic DNA, with one transposase cleaving the upper strand and one transposase cleaving the lower strand. Each of the transposon DNA in the transposome is attached to the double stranded genomic DNA at each end of the cut site, i.e. one transposon DNA of the transposome is attached to the left hand cut site and the other transposon DNA of the transposome is attached to the right hand cut site. When the transposon DNA of the transposome each have different primer binding site sequences, the left hand cut site and the right hand cut site are "barcoded" with a different and unique barcode, i.e. priming site, sequences. When the transposon DNA of the transposome each have the same primer binding site sequence, the left hand cut site and the right hand cut site are "barcoded" with the same barcode. i.e. priming site, sequence. When adjacent transposomes used to make a fragment each have a different and unique primer binding site sequence, the resulting fragment will have a different and unique primer binding site on each end of the fragment. According to certain aspects, a plurality of transposase/transposon DNA complex dimers, i.e. transposomes, bind to a corresponding plurality of target locations along a double stranded genomic DNA, for example, and then cleave the double stranded genomic DNA into a plurality of double stranded fragments with each fragment having transposon DNA with a different barcode sequence attached at each end of the double stranded fragment.

According to one aspect, the transposon DNA is attached to the double stranded genomic DNA and a single stranded gap exists between one strand of the genomic DNA and one strand of the transposon DNA. According to one aspect, gap extension is carried out to fill the gap and create a double stranded connection between the double stranded genomic DNA and the double stranded transposon DNA. According to one aspect, a nucleic acid sequence including the transposase binding site and the priming site sequence is attached at each end of the double stranded fragment. According to certain aspects, the transposase is attached to the transposon DNA which is attached at each end of the double stranded fragment. According to one aspect, the transposases are removed from the transposon DNA which is attached at each end of the double stranded genomic DNA fragments.

According to one aspect of the present disclosure, the double stranded genomic DNA fragments which have the transposon DNA with different priming site sequences attached at each end of the double stranded genomic DNA fragments are then gap filled and extended using the transposon DNA as a template. Accordingly, a double stranded nucleic acid extension product is produced which includes the double stranded genomic DNA fragment and a double stranded transposon DNA including a different priming site sequence at each end of the double stranded genomic DNA.

At this stage, the double stranded nucleic acid extension products including the genomic DNA fragment, the different priming site sequences at each end can be amplified using methods known to those of skill in the art to produce amplicons of the genomic DNA fragment and the different primer binding site at each end. PCR primer sequences and reagents can be used for amplification. The transposons as described herein may also include an RNA polymerase binding site for production of RNA transcripts which may then be reverse transcribed into cDNA for linear amplification. The double stranded nucleic acid extension products including the genomic DNA fragment and the different priming site sequences at each end can be combined with amplification reagents and the double stranded genomic nucleic acid fragment may then be amplified using methods known to those of skill in the art to produce amplicons of the double stranded genomic nucleic acid fragment.

The amplicons can then be collected and/or purified prior to further analysis. The amplicons can be sequenced using methods known to those of skill in the art. Once sequenced, the sequences can be computationally analyzed to identify the genomic DNA.

Embodiments of the present disclosure are directed to a method of amplifying DNA using multiplex end-tagging, wherein the DNA is a small amount of genomic DNA or a limited amount of DNA such as a genomic sequence or genomic sequences obtained from a single cell or a plurality of cells of the same cell type or from a tissue, fluid or blood sample obtained from an individual or a substrate. According to certain aspects of the present disclosure, the methods described herein can be performed in a single tube to create the fragments having different and unique sequences at each end which are then amplified and sequenced using high throughput sequencing platforms known to those of skill in the art.

The transposome fragmentation and barcoding method described herein is useful for amplifying and then sequencing of small or limited amounts of DNA. Methods described herein have particular application in biological systems or tissue samples characterized by highly heterogeneous cell populations such as tumor and neural masses. The methods described herein can utilize varied sources of DNA materials, including genetically heterogeneous tissues (e.g. cancers), rare and precious samples (e.g. embryonic stem cells), and non-dividing cells (e.g. neurons) and the like, as well as, sequencing platforms and genotyping methods known to those of skill in the art.

Further features and advantages of certain embodiments of the present disclosure will become more fully apparent in the following description of the embodiments and drawings thereof, and from the claims.

BRIEF DESCRIPTION OF THE DRAWINGS

The foregoing and other features and advantages of the present invention will be more fully understood from the following detailed description of illustrative embodiments taken in conjunction with the accompanying drawings in which.

DETAILED DESCRIPTION

Figure 1:
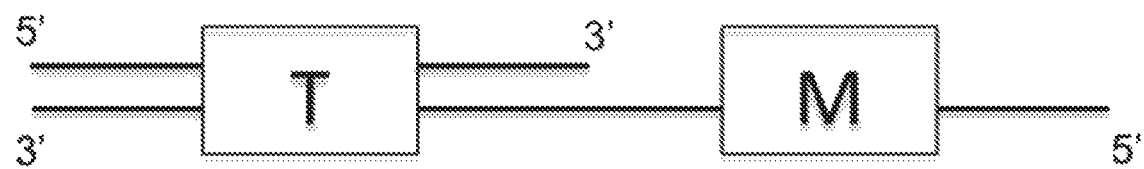
FIG. 1 depicts in schematic a structure of a transposon DNA with a 5' extension being linear, where T is the double stranded transposase binding site, and M is a multiplex priming site at one end of the extension.

The practice of certain embodiments or features of certain embodiments may employ, unless otherwise indicated, conventional techniques of molecular biology, microbiology, recombinant DNA, and so forth which are within ordinary skill in the art. Such techniques are explained fully in the literature. See e.g., Sambrook, Fritsch, and Maniatis, MOLECULAR CLONING: A LABORATORY MANUAL, Second Edition (1989). OLIGONUCLEOTIDE SYNTHESIS (M. J. Gait Ed., 1984), ANIMAL CELL CULTURE (R. 1. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOLOGY (F. M. Ausubel, R. Brent, R. E. Kingston, D. D. Moore, J. G. Siedman, J. A. Smith, and K. Struhl, eds., 1987), CURRENT PROTOCOLS IN IMMUNOLOGY (J. E. Coligan, A. M. Kruisbeek, D. H. Margulies. E. M. Shevach and W. Strober, eds., 1991); ANNUAL REVIEW OF IMMUNOLOGY; as well as monographs in journals such as ADVANCES IN IMMUNOLOGY. All patents, patent applications, and publications mentioned herein, both supra and infra, are hereby incorporated herein by reference.

Terms and symbols of nucleic acid chemistry, biochemistry, genetics, and molecular biology used herein follow those of standard treatises and texts in the field, e.g., Kornberg and Baker, *DNA Replication*, Second Edition (W.H. Freeman. New York, 1992); Lehninger, *Biochemistry*, Second Edition (Worth Publishers. New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor. *Oligonucleotide Synthesis: A Practical Approach* (IRL Press. Oxford, 1984); and the like.

The present invention is based in part on the discovery of methods for making nucleic acid fragment templates, such as from DNA or genomic DNA, using a transposase or transposome to fragment the original or starting nucleic acid sequence, such as genomic DNA, and to attach a different priming site sequence to each end of a cut or fragmentation site to thereby produce a set of fragments with each member of the set having two unique and different priming site sequences. The nucleic acid fragment templates are amplified to produce amplicons. The amplicons of the nucleic acid fragment templates may be collected and sequenced. The collected amplicons form a library of amplicons of the fragments of the original nucleic acid, such as genomic DNA.

According to one aspect, a genomic DNA, such as genomic nucleic acid obtained from a lysed single cell, is obtained. A plurality or library of transposomes is used to cut the genomic DNA into double stranded fragments. Each transposome of the plurality or library is a dimer of a transposase bound to a transposon DNA, i.e. each transposome includes two separate transposon DNA. Each transposon DNA of a transposome includes a transposase binding site and a primer binding site sequence. The primer binding site sequence is unique to the transposome. According to one aspect, the priming site sequence of each transposon of a transposome could be unique and/or different. According to one aspect, the priming site sequence of each transposon of a transposome could be the same. According to one aspect, the majority of the transposome has two transposon DNA that has different priming site sequences and only a small fraction of the transposome has two transposon DNA that has the same priming site sequence. According to one aspect, the priming site sequence of the two transposon DNA of each transposome member can be the same, but the priming site sequence or sequences of the transposon DNA from different transposome members are unique and different.

According to one aspect, the priming site sequences of each transposon DNA of a transposome is unique and different. According to one aspect, the priming site sequence or sequences of the transposon DNA of a transposome is unique and different from the remaining members of the transposome plurality or library. According to one aspect, each transposome of the plurality or library of transposomes has its own unique and different priming site sequences which are different from the remaining members of the transposome plurality or library and may have two unique and different priming site sequences which are different from the remaining members of the transposome plurality or library. The transposon DNA becomes attached to the upper and lower strands of each double stranded fragment at each cut or fragmentation site. Since the priming site sequence may be different for each transposon DNA, the cut or fragmentation site is tagged with different priming site sequences. Since the priming site sequence may be the same for each transposon DNA, the cut or fragmentation site is tagged with the same priming site sequence. Where adjacent transposomes used to generate a fragment each have different primer binding site sequences associated therewith, the fragment has different primer binding site sequences at each end of the fragment. Accordingly, the fragment will have two unique and different primer binding site sequences. Since each transposome has its own unique and/or different priming site sequence associated therewith (and may have two unique and/or different priming site sequences associated therewith), and a library of transposomes are used to create many cut or fragmentation sites, each cut or fragmentation site will have a different and unique priming site sequence attached at either end of the cut site and each fragment will have different and/or unique priming site sequences on each end of the fragment. Accordingly, many fragments from the original nucleic acid sequence are created by the library of transposomes with each fragment having a dissimilar priming site sequence at each end of the fragment. The double stranded fragments are then processed to fill gaps. The fragments are amplified using suitable amplification reagents, such as a primer sequences, DNA polymerase and nucleotides for PCR amplification and are sequenced using methods known to those of skill in the art.

DNA fragment templates made using the transposase methods described herein can be amplified within microdroplets using methods known to those of skill in the art. Microdroplets may be formed as an emulsion of an oil phase and an aqueous phase. An emulsion may include aqueous droplets or isolated aqueous volumes within a continuous oil phase Emulsion whole genome amplification methods are described using small volume aqueous droplets in oil to isolate each fragment for uniform amplification of a single cell's genome. By distributing each fragment into its own droplet or isolated aqueous reaction volume, each droplet is allowed to reach saturation of DNA amplification. The amplicons within each droplet are then merged by demulsification resulting in an even amplification of all of the fragments of the whole genome of the single cell.

In certain aspects, amplification is achieved using PCR. PCR is a reaction in which replicate copies are made of a target polynucleotide using a pair of primers or a set of primers consisting of an upstream and a downstream primer, and a catalyst of polymerization, such as a DNA polymerase, and typically a thermally-stable polymerase enzyme. Methods for PCR are well known in the art, and taught, for example in MacPherson et al. (1991) PCR 1: A Practical Approach (IRL Press at Oxford University Press). The term "polymerase chain reaction" ("PCR") of Mullis (U.S. Pat. Nos. 4,683,195, 4,683,202, and 4,965,188) refers to a method for increasing the concentration of a segment of a target sequence without cloning or purification. This process for amplifying the target sequence includes providing oligonucleotide primers with the desired target sequence and amplification reagents, followed by a precise sequence of thermal cycling in the presence of a polymerase (e.g., DNA polymerase). The primers are complementary to their respective strands ("primer binding sequences") of the double stranded target sequence. To effect amplification, the double stranded target sequence is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR") and the target sequence is said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself within each microdroplet are, themselves, efficient templates for subsequent PCR amplifications. Methods and kits for performing PCR are well known in the art. All processes of producing replicate copies of a polynucleotide, such as PCR or gene cloning, are collectively referred to herein as replication. A primer can also be used as a probe in hybridization reactions, such as Southern or Northern blot analyses.

The expression "amplification" or "amplifying" refers to a process by which extra or multiple copies of a particular polynucleotide are formed. Amplification includes methods such as PCR, ligation amplification (or ligase chain reaction, LCR) and other amplification methods. These methods are known and widely practiced in the art. See, e.g., U.S. Pat. Nos. 4,683,195 and 4,683,202 and Innis et al., "PCR protocols: a guide to method and applications" Academic Press, Incorporated (1990) (for PCR); and Wu et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization. i.e. each primer is specifically designed to be complementary to each strand of the genomic locus to be amplified.

Reagents and hardware for conducting amplification reactions are commercially available. Primers useful to amplify sequences from a particular gene region are preferably complementary to, and hybridize specifically to sequences in the target region or in its flanking regions and can be prepared using methods known to those of skill in the art. Nucleic acid sequences generated by amplification can be sequenced directly.

When hybridization occurs in an antiparallel configuration between two single-stranded polynucleotides, the reaction is called "annealing" and those polynucleotides are described as "complementary". A double-stranded polynucleotide can be complementary or homologous to another polynucleotide, if hybridization can occur between one of the strands of the first polynucleotide and the second. Complementarity or homology (the degree that one polynucleotide is complementary with another) is quantifiable in terms of the proportion of bases in opposing strands that are expected to form hydrogen bonding with each other, according to generally accepted base-pairing rules.

The terms "PCR product," "PCR fragment." and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" may refer to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.). Amplification methods include PCR methods known to those of skill in the art and also include rolling circle amplification (Blanco et al., J. Biol. Chem., 264, 8935-8940, 1989), hyperbranched rolling circle amplification (Lizard et al., Nat. Genetics, 19, 225-232, 1998), and loop-mediated isothermal amplification (Notomi et al., Nuc. Acids Res., 28, e63, 2000) each of which are hereby incorporated by reference in their entireties.

For emulsion PCR, an emulsion PCR reaction is created by vigorously shaking or stirring a "water in oil" mix to generate millions of micron-sized aqueous compartments. Microfluidic chips may be equipped with a device to create an emulsion by shaking or stirring an oil phase and a water phase. Alternatively, aqueous droplets may be spontaneously formed by combining a certain oil with an aqueous phase or introducing an aqueous phase into an oil phase. The DNA library to be amplified is mixed in a limiting dilution prior to emulsification. The combination of compartment size, i.e. microdroplet size, and amount of microdroplets created limiting dilution of the DNA fragment library to be amplified is used to generate compartments containing, on average, just one DNA molecule. Depending on the size of the aqueous compartments generated during the microdroplet formation or emulsification step, up to $3 \times 10^9$ individual PCR reactions per Ill can be conducted simultaneously in the same tube. Essentially each little aqueous compartment microdroplet in the emulsion forms a micro PCR reactor. The average size of a compartment in an emulsion ranges from sub-micron in diameter to over a 100 microns, or from 1 picoliter to 1000 picoliters or from 1 nanoliter to 1000 nanoliters or from 1 picoliter to 1 nanoliter or from 1 picoliter to 1000 nanoliters depending on the emulsification conditions.

Other amplification methods, as described in British Patent Application No. GB 2,202,328, and in PCT Patent Application No. PCT/US89/01025, each incorporated herein by reference, may be used in accordance with the present disclosure. In the former application, "modified" primers are used in a PCR-like template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other suitable amplification methods include "race and "one-sided PCR.". (Frohman, In: PCR Protocols: A Guide To Methods And Applications, Academic Press. N.Y., 1990, each herein incorporated by reference). Methods based on ligation of two (or more) oligonucleotides in the presence of nucleic acid having the sequence of the resulting "di-oligonucleotide," thereby amplifying the di-oligonucleotide, also may be used to amplify DNA in accordance with the present disclosure (Wu et al., Genomics 4:560-569, 1989, incorporated herein by reference).

According to certain aspects, an exemplary transposon system includes Tn5 transposase, Mu transposase, Tn7 transposase or IS5 transposase and the like. Other useful transposon systems are known to those of skill in the art and include Tn3 transposon system (see Maekawa, T., Yanagihara, K., and Ohtsubo. E. (1996), A cell-free system of Tn3 transposition and transposition immunity, *Genes Cells* 1, 1007-1016), Tn7 transposon system (see Craig, N. L. (1991). Tn7: a target site-specific transposon. *Mol. Microbiol.* 5, 2569-2573), Tn10 tranposon system (see Chalmers, R., Sewitz, S., Lipkow, K., and Crellin, P. (2000), Complete nucleotide sequence of Tn10, *J. Bacteriol* 182, 2970-2972), Piggybac transposon system (see Li, X., Burnight. E. R., Cooney, A. L., Malani, N., Brady. T., Sander, J. D., Staber, J., Wheelan, S. J., Joung, J. K., McCray, P. B., Jr., et al. (2013), PiggyBac transposase tools for genome engineering, *Proc. Natl. Acad. Sci. USA* 110, E2279-2287), Sleeping beauty transposon system (see Ivics, Z., Hackett, P. B., Plasterk, R. H., and Izsvak, Z. (1997), Molecular reconstruction of Sleeping Beauty, a Tcl-like transposon from fish, and its transposition in human cells, *Cell* 91, 501-510), Tol2 transposon system (see Kawakami, K. (2007). Tol2: a versatile gene transfer vector in vertebrates, *Genome Biol.* 8 Suppl. 1. S7.) DNA to be amplified may be obtained from a single cell or a small population of cells.

Methods described herein allow DNA to be amplified from any species or organism in a reaction mixture, such as a single reaction mixture carried out in a single reaction vessel. In one aspect, methods described herein include sequence independent amplification of DNA from any source including but not limited to human, animal, plant, yeast, viral, eukaryotic and prokaryotic DNA.

According to one aspect, a method of single cell whole genome amplification, sequencing and assembly is provided which includes contacting double stranded genomic DNA from a single cell with Tn5 transposases each bound to a transposon DNA, wherein the transposon DNA includes a double-stranded 19 bp transposase (Tnp) binding site and a first nucleic acid sequence including a unique and different priming site sequence to form a transposase/transposon DNA complex dimer called a transposome. The first nucleic acid sequence may be in the form of a single stranded extension. According to one aspect, the first nucleic acid sequence may be an overhang, such as a 5' overhang, wherein the overhang includes a unique and different priming site sequence. The overhang may include other functional sequences as desired. The overhang can be of any length suitable to include a priming site sequence, or other functional sequences as desired. The transposome bind to target locations along the double stranded genomic DNA and cleave the double stranded genomic DNA into a plurality of double stranded fragments, with each double stranded fragment having a first complex attached to an upper strand by the Tnp binding site and a second complex attached to a lower strand by the Tnp binding site. The transposon binding site, and therefore the transposon DNA along with the primer binding site, is attached to each 5' end of the double stranded fragment. According to one aspect, the Tn5 transposases are removed from the complex. The double stranded fragments are extended along the transposon DNA to make a double stranded extension product having dissimilar or different or unique priming site sequences at each end of the double stranded extension product. According to one aspect, a gap which may result from attachment of the Tn5 transposase binding site to the double stranded genomic DNA fragment may be filled. The gap filled double stranded extension product is mixed with amplification reagents, and the double stranded genomic DNA fragment is amplified. The amplicons, which include a dissimilar or different or unique priming site sequence (which may function as a barcode sequence) at each end, are sequenced using, for example, high-throughput sequencing methods known to those of skill in the art.

In a particular aspect, embodiments are directed to methods for the amplification, sequencing and assembly of substantially the entire genome without loss of representation of specific sites (herein defined as "whole genome amplification"). In a specific embodiment, whole genome amplification comprises amplification of substantially all fragments or all fragments of a genomic library. In a further specific embodiment, "substantially entire" or "substantially all" refers to about 80%, about 85%, about 90%, about 95%, about 97%, or about 99% of all sequences in a genome.

According to one aspect, the DNA sample is genomic DNA, micro dissected chromosome DNA, yeast artificial chromosome (YAC) DNA, plasmid DNA, cosmid DNA, phage DNA. P1 derived artificial chromosome (PAC) DNA, or bacterial artificial chromosome (BAC) DNA, mitochondrial DNA, chloroplast DNA, forensic sample DNA, or other DNA from natural or artificial sources to be tested. In another preferred embodiment, the DNA sample is mammalian DNA, plant DNA, yeast DNA, viral DNA, or prokaryotic DNA. In yet another preferred embodiment, the DNA sample is obtained from a human, bovine, porcine, ovine, equine, rodent, avian, fish, shrimp, plant, yeast, virus, or bacteria. Preferably the DNA sample is genomic DNA.

According to certain exemplary aspects, a transposition system is used to make nucleic acid fragments for amplification, sequencing and assembly as desired. According to one aspect, a transposition system is used to fragment genomic DNA into double stranded genomic DNA fragments with the transposon DNA having different priming site sequences inserted therein. As illustrated in FIG. 1, a transposon DNA includes a double stranded transposase binding site and a unique and different priming site sequence M. The double stranded transposase binding site may be a double-stranded 19 bp Tn5 transposase (Tnp) binding site which is linked or connected, such as by covalent bond, to a single-stranded overhang including a priming site sequence, such as at one end of the overhang. The transposon DNA is inserted into the genomic DNA of a single cell while creating fragments using a transposase. After transposase removal and gap fill-in, the genomic DNA fragments having dissimilar or different or unique priming site sequences at each end of the fragment are amplified using primers together with a DNA polymerase, nucleotides and amplification reagents to PCR amplify the whole genome of the single cell.

According to certain aspects when amplifying small amounts of DNA such as DNA from a single cell, a DNA column purification step is not carried out so as to maximize the small amount (~6 pg) of genomic DNA that can be obtained from within a single cell prior to amplification. The DNA can be amplified directly from a cell lysate or other impure condition. Accordingly, the DNA sample may be impure, unpurified, or not isolated. Accordingly, aspects of the present method allow one to maximize genomic DNA for amplification and reduce loss due fragments having the same priming site sequence on each end as with other methods, i.e. non-multiplex methods. According to an additional aspect, methods described herein may utilize amplification methods other than PCR.

Figure 2:
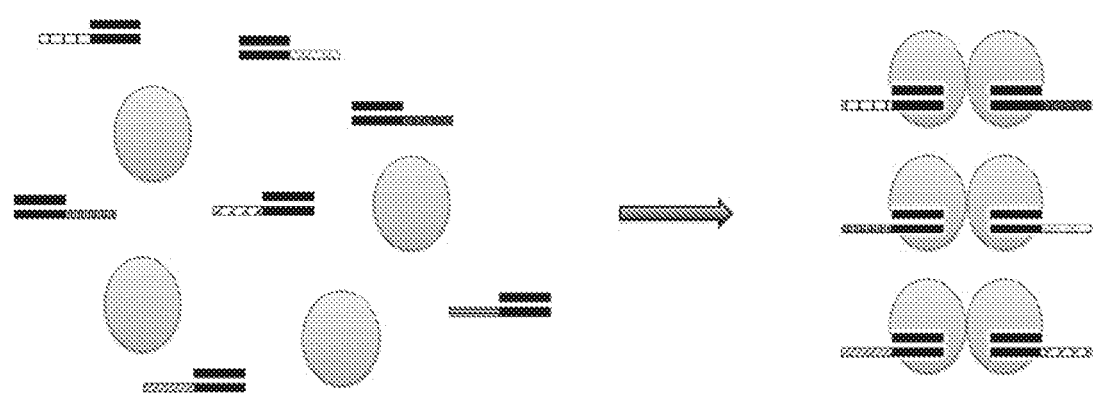
FIG. 2 is a schematic of a general embodiment of transposase and transposon DNA spontaneously forming a transposome, which may occur within a droplet or other formation media. Prior to transposome formation, each transposon has a different and unique priming site sequence represented by different patterns. After transposome formation, each transposon of the transposome has a different and unique priming site sequence represented by different patterns.

According to one aspect and as illustrated in general in FIG. 2, transposase (Tnp, grey circles) and the transposon DNA each having unique and different priming site sequences illustrated by different pattern overhang sequences are combined to form a plurality of transposomes. Each transposome has two different and unique priming site sequences. Each transposome has two different and unique priming site sequences compared to each other transposome within the plurality.

Figure 3A:
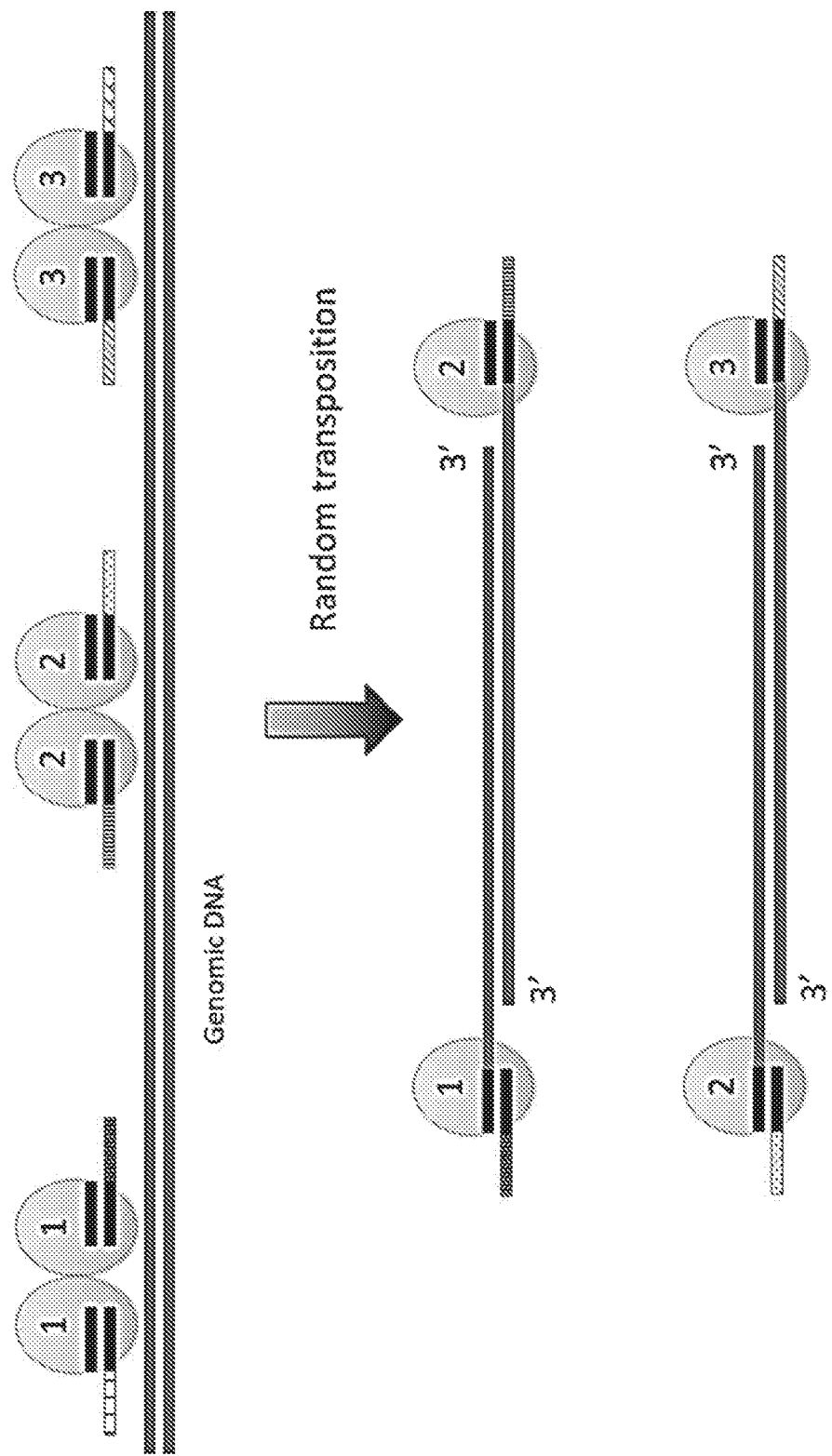
FIG. 3A is a schematic of transposome binding to genomic DNA, cutting into fragments and addition or insertion of transposon DNA including a transposase binding site (black) and a unique and different priming site sequence on each transposon of each transposome as represented in each transposome by different patterns.

As shown in FIG. 3A, the transposomes of the transposome library randomly capture or otherwise bind to the target single-cell genomic DNA as dimers. Representative transposomes are numbered 1, 2 and 3, though the number of transposome members can be greater depending on the desired application. A representative number of transposons having different and/or unique primer binding site sequences is between 5 and 50. Each transposome includes two unique and/or different priming site sequences. For example, transposome 1 includes two unique and/or different priming site sequences, transposome 2 includes two unique and/or different priming site sequences, transposome 3 includes two unique and/or different priming site sequences, etc. The unique and/or different priming site sequence is within each transposon DNA of the transposome. The transposases in the transposome cut the genomic DNA with one transposase cutting an upper strand and one transposase cutting a lower strand to create a genomic DNA fragment. The plurality of transposomes creates a plurality of genomic DNA fragments. One transposon DNA from the transposon DNA dimer is thus attached to each end of the cut site or fragmentation site, i.e., one transposon DNA from transposome 1 is attached to the left hand cut site and the other transposon DNA from transposome 1 is attached to the right hand cut site. Since the transposome library cuts the nucleic acid into fragments, each fragment will have a dissimilar priming site sequence at each end of the fragment. This is represented by the two exemplary fragments where the upper fragment has unique and different priming site sequence 1 on one end and unique and different priming site sequence 2 on the other end. Likewise, the lower fragment has unique and different priming site sequence 2 on one end and unique and different priming site sequence 3 on the other end. As illustrated, the cut site between the two fragments is produced by transposome 2 and the left hand cut site (i.e. viewing the right side of the upper fragment in FIG. 3A) includes the one transposon with unique and different priming site sequence 2 while the right hand cut site (i.e. viewing the left side of the lower fragment in FIG. 3A) includes unique and different priming site sequence 2 (with "2" referring to transposome 2).

Figure 3B:
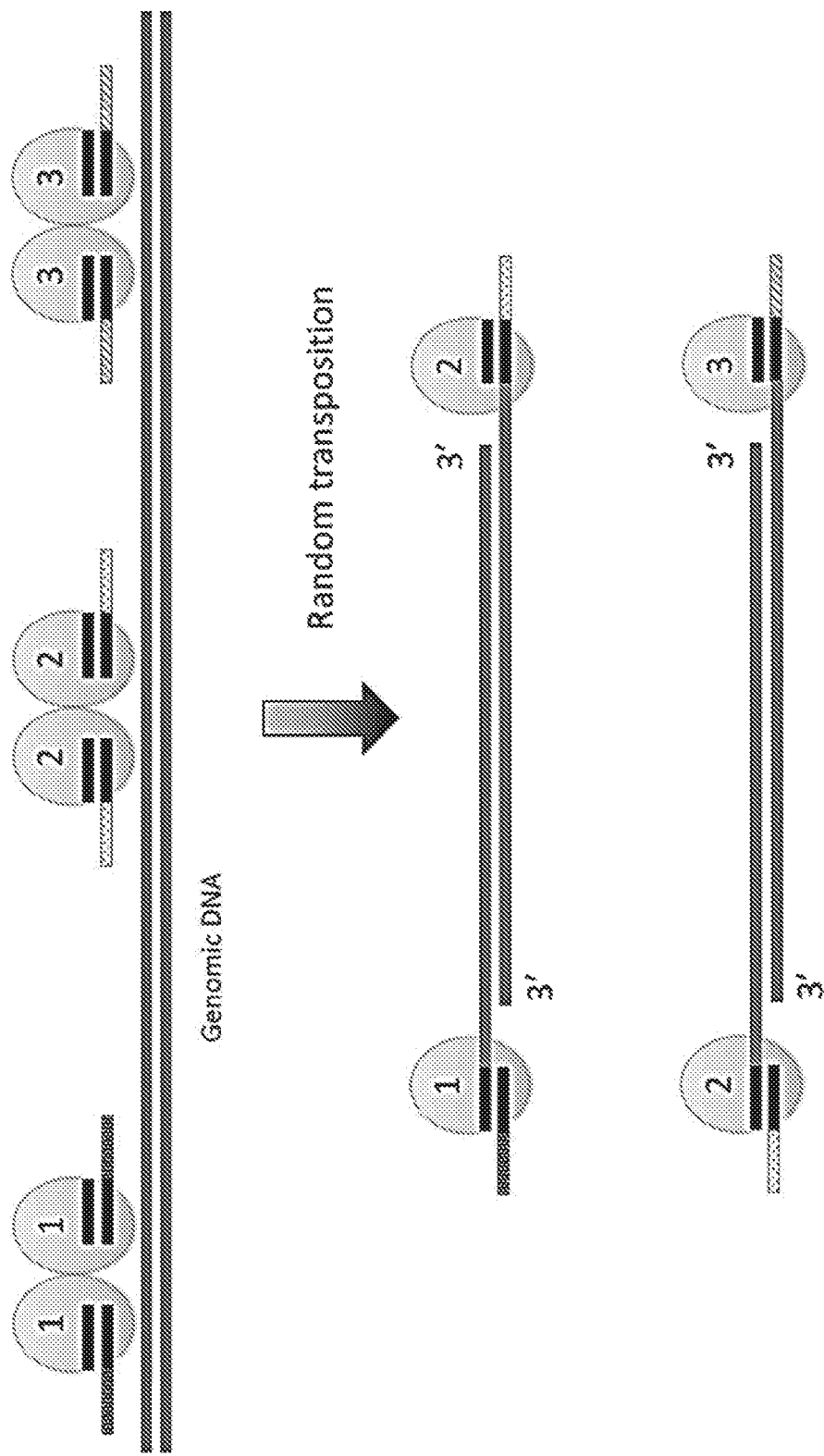
FIG. 3B is a schematic of transposome binding to genomic DNA, cutting into fragments and addition or insertion of transposon DNA including a transposase binding site (black) and a unique and different priming site sequence representative of the transposome. i.e. the same unique and different primer binding site sequence is present on each transposon of the transposome, as represented in each transposome by the same pattern. The different primer binding site sequences between each transposome are represented by different patterns.

As shown in FIG. 3B, the transposomes of the transposome library randomly capture or otherwise bind to the target single-cell genomic DNA as dimers. Representative transposomes are numbered 1, 2 and 3, though the number of transposome members can be greater depending on the desired application. A representative number of transposons having different and/or unique primer binding site sequences is between 5 and 50. Each transposome includes the same unique and/or different primer binding site sequence at each transposon of the transposome. For example, transposome 1 includes the same primer binding site sequence on each transposon, transposome 2 includes the same primer binding site sequence on each transposon, transposome 3 includes the same primer binding site sequence on each transposon, etc. However, each transposome has a unique and different primer binding site associated therewith, such that each transposome has a different primer binding site associated therewith compared to other members of the transposome library. The transposases in the transposome cut the genomic DNA with one transposase cutting an upper strand and one transposase cutting a lower strand to create a genomic DNA fragment. The plurality of transposomes creates a plurality of genomic DNA fragments. One transposon DNA from the transposon DNA dimer is thus attached to each end of the cut site or fragmentation site, i.e., one transposon DNA from transposome 1 is attached to the left hand cut site and the other transposon DNA from transposome 1 is attached to the right hand cut site. Since the transposome library cuts the nucleic acid into fragments, each fragment will have a dissimilar priming site sequence at each end of the fragment, since adjacent transposomes bound to the nucleic acid which create the fragment each have different primer binding site sequences. This is represented by the two exemplary fragments where the upper fragment has unique and different priming site sequence 1 on one end and unique and different priming site sequence 2 on the other end. Likewise, the lower fragment has unique and different priming site sequence 2 on one end (which is the same primer binding site sequence as on the right end of the upper fragment) and unique and different priming site sequence 3 on the other end. As illustrated, the cut site between the two fragments is produced by transposome 2 and the left hand cut site (i.e. viewing the right side of the upper fragment in FIG. 3B) includes the one transposon with unique and different priming site sequence 2 while the right hand cut site (i.e. viewing the left side of the lower fragment in FIG. 3B) includes unique and different priming site sequence 2 (with "2" referring to transposome 2). Accordingly, even where the transposome has the same primer binding site sequence on each transposon, the method results in a fragment having different primer binding site sequences at each end of the fragment.

Figure 4:
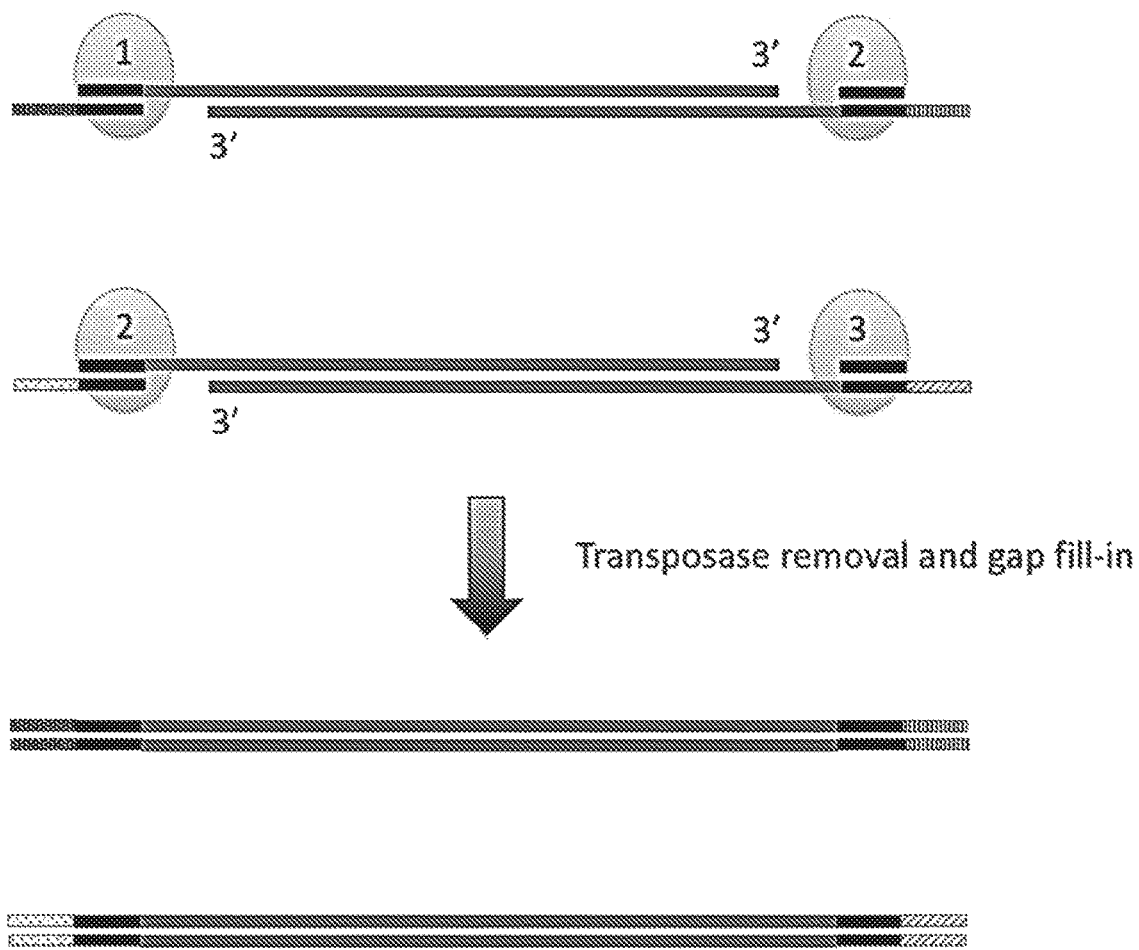
FIG. 4 is a schematic of transposase removal, gap filling to form nucleic acid extension products including genomic DNA, transposase binding site and a unique and different priming site sequence on each end of the extension product.

As illustrated in FIG. 4, the fragmentation of the genomic DNA leaves a gap on both ends of the transposition/insertion site. The gap may have any length but a 9 base gap is exemplary. The result is a genomic DNA fragment with a transposon DNA Tnp binding site attached to the 5' position of an upper strand and a transposon DNA Tnp binding site attached to the 5' position of a lower strand. Gaps resulting from the attachment or insertion of the transposon DNA are shown. After transposition, the transposase is removed and gap extension is performed to fill the gap and complement the single-stranded overhang originally designed in the transposon DNA as shown in FIG. 4.

Figure 5:
FIG. 5 is a schematic showing multiplex PCR amplification of the fragments of FIG. 4.
Figure 5:
Figure 5:
Figure 5:
Figure 5:
Figure 5:
Figure 5:
Figure 5:
Figure 5:

As further illustrated in FIG. 5, the fragments shown in FIG. 4 are subject to multiplex PCR amplification to produce amplicons.

Particular Tn5 transposition systems are described and are available to those of skill in the art. See Goryshin, I. Y. and W. S. Reznikoff. *Tn5 in vitro transposition*. The Journal of biological chemistry, 1998, 273(13): p. 7367-74; Davies, D. R., et al., *Three-dimensional structure of the Tn5 synaptic complex transposition intermediate*. Science, 2000, 289 (5476): p. 77-85; Goryshin. I. Y., et al., *Insertional transposon mutagenesis by electroporation of released Tn5 transposition complexes*. Nature biotechnology, 2000, 18(1): p. 97-100 and Steiniger-White, M., 1. Rayment, and W. S. Reznikoff. *Structure/function insights into Tn5 transposition*. Current opinion in structural biology, 2004, 14(1): p. 50-7 each of which are hereby incorporated by reference in their entireties for all purposes. Kits utilizing a Tn5 transposition system for DNA library preparation and other uses are known. See Adey, A., et al., *Rapid, low-input, low-bias construction of shotgun fragment libraries by high-density in vitro transposition*. Genome biology, 2010, 11(12): p. R119; Marine, R., et al., *Evaluation of a transposase protocol for rapid generation of shotgun high-throughput sequencing libraries from nanogram quantities of DNA*. Applied and environmental microbiology. 2011, 77(22): p. 8071-9; Parkinson, N.J., et al., *Preparation of high-quality next-generation sequencing libraries from picogram quantities of target DNA. Genome research*, 2012, 22(1): p. 125-33; Adey, A. and J. Shendure. *Ultra-low-input, tagmentation-based whole-genome bisulfite sequencing*. Genome research, 2012, 22(6): p. 1139-43: Picelli, S., et al., *Full-length RNA-seq from single cells using Smart-seq2*. Nature protocols, 2014, 9(1): p. 171-81 and Buenrostro, J. D., et al., *Transposition of native chromatin for fast and sensitive epigenomic profiling of open chromatin, DNA-binding proteins and nucleosome position*. Nature methods. 2013, each of which is hereby incorporated by reference in its entirety for all purposes. See also WO 98/10077, EP 2527438 and EP 2376517 each of which is hereby incorporated by reference in its entirety. A commercially available transposition kit is marketed under the name NEXTERA and is available from Illumina.

The term "genome" as used herein is defined as the collective gene set carried by an individual, cell, or organelle. The term "genomic DNA" as used herein is defined as DNA material comprising the partial or full collective gene set carried by an individual, cell, or organelle.

As used herein, the term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and 2,2N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide," "oligonucleotide" and "nucleic acid molecule" are used interchangeably herein and refer to a polymer of nucleotides, either deoxyribonucleotides or ribonucleotides, of any length joined together by a phosphodiester linkage between 5' and 3' carbon atoms. Polynucleotides can have any three-dimensional structure and can perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. The term also refers to both double- and single-stranded molecules. Unless otherwise specified or required, any embodiment of this invention that comprises a polynucleotide encompasses both the double-stranded form and each of two complementary single-stranded forms known or predicted to make up the double-stranded form. A polynucleotide is composed of a specific sequence of four nucleotide bases: adenine (A); cytosine (C); guanine (G); thymine (T); and uracil (U) for thymine when the polynucleotide is RNA. Thus, the term polynucleotide sequence is the alphabetical representation of a polynucleotide molecule. This alphabetical representation can be input into databases in a computer having a central processing unit and used for bioinformatics applications such as functional genomics and homology searching.

The terms "DNA," "DNA molecule" and "deoxyribonucleic acid molecule" refer to a polymer of deoxyribonucleotides. DNA can be synthesized naturally (e.g., by DNA replication). RNA can be post-transcriptionally modified. DNA can also be chemically synthesized. DNA can be single-stranded (i.e., ssDNA) or multi-stranded (e.g., double stranded, i.e., dsDNA).

The terms "nucleotide analog," "altered nucleotide" and "modified nucleotide" refer to a non-standard nucleotide, including non-naturally occurring ribonucleotides or deoxyribonucleotides. In certain exemplary embodiments, nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.: the 6 position, e.g., 6-(2-amino) propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated. e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21. Rusckowski et al. Antisense Nucleic Acid Drug Dev. 2000 Oct. 10(5):333-45. Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) decrease the rate of hydrolysis of, for example, polynucleotides comprising said analogs in vivo or in vitro.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the terms "complementary" and "complementarity" are used in reference to nucleotide sequences related by the base-pairing rules. For example, the sequence 5'-AGT-3' is complementary to the sequence 5'-ACT-3'. Complementarity can be partial or total. Partial complementarity occurs when one or more nucleic acid bases is not matched according to the base pairing rules. Total or complete complementarity between nucleic acids occurs when each and every nucleic acid base is matched with another base under the base pairing rules. The degree of complementarity between nucleic acid strands has significant effects on the efficiency and strength of hybridization between nucleic acid strands.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the melting temperature of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$ (% G+C), when a nucleic acid is in aqueous solution at 1 M NaCl (See. e.g., Anderson and Young, Quantitative Filter Hybridization, in *Nucleic Acid Hybridization* (1985)). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted.

"Low stringency conditions." when used in reference to nucleic acid hybridization, comprise conditions equivalent to binding or hybridization at 42° C. in a solution consisting of 5×SSPE (43.8 g/l NaCl, 6.9 g/l NaH$_2$PO$_4$(H$_2$O) and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma)) and 100 mg/ml denatured salmon sperm DNA followed by washing in a solution comprising 5×SSPE, 0.1% SDS at 42° C. when a probe of about 500 nucleotides in length is employed.

"Medium stringency conditions," when used in reference to nucleic acid hybridization, comprise conditions equivalent to binding or hybridization at 42° C. in a solution consisting of 5×SSPE (43.8 g/l NaCl. 6.9 g/l NaH$_2$PO$_4$ (H$_2$O) and 1.85 g/l EDTA. pH adjusted to 7.4 with NaOH), 0.5% SDS. 5×Denhardt's reagent and 100 mg/ml denatured salmon sperm DNA followed by washing in a solution comprising 1.0×SSPE. 1.0% SDS at 42° C. when a probe of about 500 nucleotides in length is employed.

"High stringency conditions," when used in reference to nucleic acid hybridization, comprise conditions equivalent to binding or hybridization at 42° C. in a solution consisting of 5×SSPE (43.8 g/l NaCl, 6.9 g/l NaH$_2$PO$_4$(H$_2$O) and 1.85 g/l EDTA, pH adjusted to 7.4 with NaOH), 0.5% SDS. 5×Denhardt's reagent and 100 mg/ml denatured salmon sperm DNA followed by washing in a solution comprising 0.1×SSPE. 1.0% SDS at 42° C. when a probe of about 500 nucleotides in length is employed.

In certain exemplary embodiments, cells are identified and then a single cell or a plurality of cells is isolated. Cells within the scope of the present disclosure include any type of cell where understanding the DNA content is considered by those of skill in the art to be useful. A cell according to the present disclosure includes a cancer cell of any type, hepatocyte, oocyte, embryo, stem cell, iPS cell, ES cell, neuron, erythrocyte, melanocyte, astrocyte, germ cell, oligodendrocyte, kidney cell and the like. According to one aspect, the methods of the present invention are practiced with the cellular DNA from a single cell. A plurality of cells includes from about 2 to about 1,000,000 cells, about 2 to about 10 cells, about 2 to about 100 cells, about 2 to about 1,000 cells, about 2 to about 10,000 cells, about 2 to about 100,000 cells, about 2 to about 10 cells or about 2 to about 5 cells.

Nucleic acids processed by methods described herein may be DNA and they may be obtained from any useful source, such as, for example, a human sample. In specific embodiments, a double stranded DNA molecule is further defined as comprising a genome, such as, for example, one obtained from a sample from a human. The sample may be any sample from a human, such as blood, serum, plasma, cerebrospinal fluid, cheek scrapings, nipple aspirate, biopsy, semen (which may be referred to as ejaculate), urine, feces, hair follicle, saliva, sweat, immunoprecipitated or physically isolated chromatin, and so forth. In specific embodiments, the sample comprises a single cell. In specific embodiments, the sample includes only a single cell.

In particular embodiments, the amplified and assembled nucleic acid molecule from the sample provides diagnostic or prognostic information. For example, the prepared nucleic acid molecule from the sample may provide genomic copy number and/or sequence information, allelic variation information, cancer diagnosis, prenatal diagnosis, paternity information, disease diagnosis, detection, monitoring, and/or treatment information, sequence information, and so forth.

As used herein, a "single cell" refers to one cell. Single cells useful in the methods described herein can be obtained from a tissue of interest, or from a biopsy, blood sample, or cell culture. Additionally, cells from specific organs, tissues, tumors, neoplasms, or the like can be obtained and used in the methods described herein. Furthermore, in general, cells from any population can be used in the methods, such as a population of prokaryotic or eukaryotic single celled organisms including bacteria or yeast. A single cell suspension can be obtained using standard methods known in the art including, for example, enzymatically using trypsin or papain to digest proteins connecting cells in tissue samples or releasing adherent cells in culture, or mechanically separating cells in a sample. Single cells can be placed in any suitable reaction vessel in which single cells can be treated individually. For example a 96-well plate, such that each single cell is placed in a single well.

Methods for manipulating single cells are known in the art and include fluorescence activated cell sorting (FACS), flow cytometry (Herzenberg., PNAS USA 76:1453-55 1979), micromanipulation and the use of semi-automated cell pickers (e.g. the Quixell™ cell transfer system from Stoelting Co.). Individual cells can, for example, be individually selected based on features detectable by microscopic observation, such as location, morphology, or reporter gene expression. Additionally, a combination of gradient centrifugation and flow cytometry can also be used to increase isolation or sorting efficiency.

Once a desired cell has been identified, the cell is lysed to release cellular contents including DNA, using methods known to those of skill in the art. The cellular contents are contained within a vessel or a collection volume. In some aspects of the invention, cellular contents, such as genomic DNA, can be released from the cells by lysing the cells. Lysis can be achieved by, for example, heating the cells, or by the use of detergents or other chemical methods, or by a combination of these. However, any suitable lysis method known in the art can be used. For example, heating the cells at 72° C. for 2 minutes in the presence of Tween-20 is sufficient to lyse the cells. Alternatively, cells can be heated to 65° C. for 10 minutes in water (Esumi et al., *Neurosci Res* 60(4):439-51 (2008)); or 70° C. for 90 seconds in PCR buffer II (Applied Biosystems) supplemented with 0.5% NP-40 (Kurimoto et al., *Nucleic Acids Res* 34(5):e42 (2006)); or lysis can be achieved with a protease such as Proteinase K or by the use of chaotropic salts such as guanidine isothiocyanate (U.S. Publication No. 2007/0281313). Amplification of genomic DNA according to methods described herein can be performed directly on cell lysates, such that a reaction mix can be added to the cell lysates. Alternatively, the cell lysate can be separated into two or more volumes such as into two or more containers, tubes or regions using methods known to those of skill in the art with a portion of the cell lysate contained in each volume container, tube or region. Genomic DNA contained in each container, tube or region may then be amplified by methods described herein or methods known to those of skill in the art.

A nucleic acid used in the invention can also include native or non-native bases. In this regard a native deoxyribonucleic acid can have one or more bases selected from the group consisting of adenine, thymine, cytosine or guanine and a ribonucleic acid can have one or more bases selected from the group consisting of uracil, adenine, cytosine or guanine. Exemplary non-native bases that can be included in a nucleic acid, whether having a native backbone or analog structure, include, without limitation, inosine, xathanine, hypoxathanine, isocytosine, isoguanine. 5-methylcytosine. 5-hydroxymethyl cytosine. 2-aminoadenine. 6-methyl adenine. 6-methyl guanine. 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine. 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. A particular embodiment can utilize isocytosine and isoguanine in a nucleic acid in order to reduce non-specific hybridization, as generally described in U.S. Pat. No. 5,681,702.

As used herein, the term "primer" generally includes an oligonucleotide, either natural or synthetic, that is capable, upon forming a duplex with a polynucleotide template, of acting as a point of initiation of nucleic acid synthesis, such as a sequencing primer, and being extended from its 3' end along the template so that an extended duplex is formed. The sequence of nucleotides added during the extension process is determined by the sequence of the template polynucleotide. Usually primers are extended by a DNA polymerase. Primers usually have a length in the range of between 3 to 36 nucleotides, also 5 to 24 nucleotides, also from 14 to 36 nucleotides. Primers within the scope of the invention include orthogonal primers, amplification primers, constructions primers and the like. Pairs of primers can flank a sequence of interest or a set of sequences of interest. Primers and probes can be degenerate or quasi-degenerate in sequence. Primers within the scope of the present invention bind adjacent to a target sequence. A "primer" may be considered a short polynucleotide, generally with a free 3'-OH group that binds to a target or template potentially present in a sample of interest by hybridizing with the target, and thereafter promoting polymerization of a polynucleotide complementary to the target. Primers of the instant invention are comprised of nucleotides ranging from 17 to 30 nucleotides. In one aspect, the primer is at least 17 nucleotides, or alternatively, at least 18 nucleotides, or alternatively, at least 19 nucleotides, or alternatively, at least 20 nucleotides, or alternatively, at least 21 nucleotides, or alternatively, at least 22 nucleotides, or alternatively, at least 23 nucleotides, or alternatively, at least 24 nucleotides, or alternatively, at least 25 nucleotides, or alternatively, at least 26 nucleotides, or alternatively, at least 27 nucleotides, or alternatively, at least 28 nucleotides, or alternatively, at least 29 nucleotides, or alternatively, at least 30 nucleotides, or alternatively at least 50 nucleotides, or alternatively at least 75 nucleotides or alternatively at least 100 nucleotides.

The expression "amplification" or "amplifying" refers to a process by which extra or multiple copies of a particular polynucleotide are formed.

The DNA amplified according to the methods described herein may be sequenced and analyzed using methods known to those of skill in the art. Determination of the sequence of a nucleic acid sequence of interest can be performed using a variety of sequencing methods known in the art including, but not limited to, sequencing by hybridization (SBH), sequencing by ligation (SBL) (Shendure et al. (2005) *Science* 309:1728), quantitative incremental fluorescent nucleotide addition sequencing (QIFNAS), stepwise ligation and cleavage, fluorescence resonance energy transfer (FRET), molecular beacons. TaqMan reporter probe digestion, pyrosequencing, fluorescent in situ sequencing (FISSEQ). FISSEQ beads (U.S. Pat. No. 7,425,431), wobble sequencing (PCT/US05/27695), multiplex sequencing (U.S. Ser. No. 12/027,039, filed Feb. 6, 2008; Porreca et al (2007) *Nat. Methods* 4:931), polymerized colony (POLONY) sequencing (U.S. Pat. Nos. 6,432,360, 6,485,944 and 6,511, 803, and PCT/US05/06425); nanogrid rolling circle sequencing (ROLONY) (U.S. Ser. No. 12/120,541, filed May 14, 2008), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods. e.g., using platforms such as Roche 454, Illumina Solexa, AB-SOLiD, Helicos, Polonator platforms and the like, can also be utilized. A variety of light-based sequencing technologies are known in the art (Landegren et al. (1998) *Genome Res.* 8:769-76; Kwok (2000) *Pharmacogenomics* 1:95-100: and Shi (2001) *Clin. Chem.* 47:164-172).

The amplified DNA can be sequenced by any suitable method. In particular, the amplified DNA can be sequenced using a high-throughput screening method, such as Applied Biosystems' SOLiD sequencing technology, or Illumina's Genome Analyzer. In one aspect of the invention, the amplified DNA can be shotgun sequenced. The number of reads can be at least 10.000, at least 1 million, at least 10 million, at least 100 million, or at least 1000 million. In another aspect, the number of reads can be from 10,000 to 100,000, or alternatively from 100,000 to 1 million, or alternatively from 1 million to 10 million, or alternatively from 10 million to 100 million, or alternatively from 100 million to 1000 million. A "read" is a length of continuous nucleic acid sequence obtained by a sequencing reaction.

"Shotgun sequencing" refers to a method used to sequence very large amount of DNA (such as the entire genome). In this method, the DNA to be sequenced is first shredded into smaller fragments which can be sequenced individually. The sequences of these fragments are then reassembled into their original order based on their overlapping sequences, thus yielding a complete sequence. "Shredding" of the DNA can be done using a number of difference techniques including restriction enzyme digestion or mechanical shearing. Overlapping sequences are typically aligned by a computer suitably programmed. Methods and programs for shotgun sequencing a cDNA library are well known in the art.

The amplification and sequencing methods are useful in the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining the genomic DNA in order to determine whether an individual is at risk of developing a disorder and/or disease. Such assays can be used for prognostic or predictive purposes to thereby prophylactically treat an individual prior to the onset of the disorder and/or disease. Accordingly, in certain exemplary embodiments, methods of diagnosing and/or prognosing one or more diseases and/or disorders using one or more of expression profiling methods described herein are provided.

As used herein, the term "biological sample" is intended to include, but is not limited to, tissues, cells, biological fluids and isolates thereof, isolated from a subject, as well as tissues, cells and fluids present within a subject.

In certain exemplary embodiments, electronic apparatus readable media comprising one or more genomic DNA sequences described herein is provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon one or more expression profiles described herein.

As used herein, the term "electronic apparatus" is intended to include any suitable computing or processing apparatus or other device configured or adapted for storing data or information. Examples of electronic apparatuses suitable for use with the present invention include stand-alone computing apparatus; networks, including a local area network (LAN), a wide area network (WAN) Internet, Intranet. and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising one or more expression profiles described herein.

A variety of software programs and formats can be used to store the genomic DNA information of the present invention on the electronic apparatus readable medium. For example, the nucleic acid sequence can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of data processor structuring formats (e.g., text file or database) may be employed in order to obtain or create a medium having recorded thereon one or more expression profiles described herein.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures and accompanying claims.

Example I

General Protocol

The following general protocol is useful for whole genome amplification. A single cell is lysed in lysis buffer. The transposome library including transposomes each with a different and unique primer binding site sequence (or each with two different and unique primer binding site sequences) as described herein and transposition buffer are added to the cell lysis which is mixed well and is incubated at 55° C. for 10 minutes. 1 mg/ml protease is added after the transposition to remove the transposase from binding to the single cell genomic DNA. Q5 DNA polymerase, dNTP, PCR reaction buffer and primers are added to the reaction mixture which is heated to 72° C. for 10 min to fill in the gap generated from the transposon insertion. 5 to 25 cycles of PCR reaction are performed to amplify the single cell genomic DNA. The amplification products are purified for further analysis such as by high through put deep sequencing.

Example II

Cell Lysis

A cell is selected, cut from a culture dish, and dispensed in a tube using a laser dissection microscope (LMD-6500, Leica) as follows. The cells are plated onto a membrane-coated culture dish and observed using bright field microscopy with a 10× objective (Leica). A UV laser is then used to cut the membrane around an individually selected cell such that it falls into the cap of a PCR tube. The tube is briefly centrifuged to bring the cell down to the bottom of the tube. 3-5 μl lysis buffer (30 mM Tris-Cl PH 7.8, 2 mM EDTA, 20 mM KCl. 0.2% Triton X-100, 500 μg/ml Qiagen Protease) is added to the side of the PCR tube and span down. The captured cell is then thermally lysed using the following temperature schedule on PCR machine: 50° C. 3 hours. 75° C. 30 minutes. Alternatively, mouth pipette a single cell into a low salt lysis buffer containing EDTA and protease such as QIAGEN protease (QIAGEN) at a concentration of 10-5000 μg/mL. The incubation condition varies based on the protease that is used. In the case of QIAGEN protease, the incubation would be 37-55° C. for 1-4 hrs. The protease is then heat inactivated up to 80° C. and further inactivated by specific protease inhibitors such as 4-(2-Aminoethyl) benzenesulfonyl fluoride hydrochloride (AEBSF) or phenylmethanesulfonyl fluoride (PMSF) (Sigma Aldrich). The cell lysis is preserved at −80° C.

Example III

Transposition

The single cell lysis and the transposome library are mixed in a buffer system containing 1-100 mM $Mg^{2+}$ and optionally 1-100 mM $Mn^{2+}$ or $Co^{2+}$ or $Ca^{2+}$ as well and incubate at 37-55° C. for 5-240 minutes. The reaction volume varies depending on the cell lysis volume. The amount of transposome library added in the reaction could be readily tuned depending on the desired fragmentation size. The transposition reaction is stopped by chelating $Mg^{2+}$ using EDTA and optionally EGTA or other chelating agents for ions. Optionally, short double stranded DNA could be added to the mixture as a spike-in. The residue transposome is inactivated by protease digestion such as QIAGEN protease at a final concentration 1-500 μg/mL at 37-55° C. for 10-60 minutes. The protease is then inactivated by heat and/or protease inhibitor, such as AEBSF.

Example IV

Gap Filling

After transposition and transposase removal, a PCR reaction mixture including $Mg^{2+}$, dNTP mix, primers and a thermal stable DNA polymerase such as Deepvent exo-DNA polymerase (New England Biolabs) is added to the solution at a suitable temperature and for a suitable time period to fill the 9 bp gap left by the transposition reaction. The gap filling incubation temperature and time depends on the specific DNA polymerase used. After the reaction, the DNA polymerase is optionally inactivated by heating and/or protease treatment such as QIAGEN protease. The protease, if used, is then inactivated by heat and/or protease inhibitor.

Example V

DNA Fragment Amplification

According to one aspect, general methods known to those of skill in the art are used to amplify a DNA fragment. The gap filled double stranded products from the above example including the DNA fragments with primer binding sites are added to PCR reaction reagents in an aqueous medium. The aqueous medium is then subject to PCR conditions to PCR amplify each DNA fragment.

Example VI

Sequencing of DNA Fragment Amplicons

According to one aspect, the fragments are sequenced using methods known to those of skill in the art and the sequences are stored in computer readable memory. The sequences then can be compared an assembled into genomic sequences using methods, including software methods, known to those of skill in the art.

Example VII

Whole Genome Amplification of a Single BJ Cell with a Transposome Library Containing 20 Different Transposon DNA The composition of the transposon sequence contains a double stranded Tn5 transposase binding site (T) and a single stranded 5 prime overhang functioning as a multiplex priming site (M), as shown in FIG. 1. Each type of transposon sequence has the same T region, but differs in M region. To make a pool of transposon mixtures of 20 transposon sequences, equal molar of each type of transposon sequences are mixed in a buffer containing 10 mM Tris pH=8, 50 mM NaCl and 1 mM EDTA. To assemble transposome complexes, the 20 transposon pool is mixed with Tn5 transposase at equal molar ratio and incubated at room temperature for 30 minutes (FIG. 2).

The single BJ cells are FACS sorted to 3 ul lysis buffer containing 20 mM Tris pH=8, 20 mM NaCl. 0.1% Triton X100, 15 mM DTT, 1 mM EDTA and 1 mg/ml Qiagen protease. The cells are then incubated at 50 degree for 3 hours followed by 70 degree for 30 minutes. 100 nM transposome is then added to the cell lysate and the transposition reaction mixture is incubated at 55 degree for 10 minutes with magnesium final concentration of 5 mM. After removing the transposase, the genomic DNA is cut into millions of small DNA fragments, each tagged with one of the 20 transposon sequences at each end. (FIG. 3A) In this manner, the transposome library may include 20 different and/or unique primer binding site sequences as described herein while the members of the transposome library may approach millions of members. The chance of a DNA fragment tagged by the same transposon sequence on both ends is 1/20=5%. A DNA polymerase reaction mixture containing 200 uM each dNTPs. 1×NEB Q5 reaction buffer, 125 nM each of 20 primers and 0.02 U/uL Q5 DNA polymerase is then added and incubated at 72° C. for 3 minutes to fill the gap left by the transposition (FIG. 4). 15 cycles of PCR reactions are then performed as: 98° C. 30 s. 65° C. 1 min, 72° C. 2 min as shown in FIG. 5 to amplify the target genomic DNA. The amplification products are then purified by Zymo DNA purification column.

There is a limitation, however, in the number N and the sequences of the M sites: As in the case of multiplex PCR, random annealing between primers can happen, and it becomes more likely when the number of primer sequences (N) increases, or when primer concentration increases. It is therefore necessary to choose orthogonal sequences for M, so that the primers specific to the N types of M sites do not form primer dimers.

Although those of skill in the art can readily find orthogonal primer sequences (and hence sequences for M sites) from multiplex PCR studies, one needs to ensure that the transposition of each of the 20 transposon sequences is as equally likely as possible. If transposon sequence A is more likely to be inserted into target DNA than all other sequences by around 40-fold, for instance, then the probability of having A-A on both ends of a DNA fragment will be approximately $(40/(40+N-1))^2=46\%$ for N=20. This is expected to result in a loss rate of 46%, almost betraying the original intention to avoid the 50% loss rate. To achieve orthogonality with even insertion propensity, one of skill can design orthogonal primer binding site sequences for use with transposons. For example, the following 20 transposon primer binding site sequences satisfy orthogonality. It is to be understood that many other such sets of primer binding site sequences can be designed by those of skill in the art and the following 20 transposon primer binding site sequences is not intended to be limiting in any way. The sequences are shown below (from 5' to 3'):

Transposon A:
(SEQ ID NO: 1)
AGAAGCCGTGTGCCGGTCTA,

Transposon B:
(SEQ ID NO: 2)
ATCGTGCGGACGAGACAGCA,

Transposon C:
(SEQ ID NO: 3)
AATCCTAGCACCGGTTCGCC,

Transposon D:
(SEQ ID NO: 4)
ACGTGTTGCAGGTGCACTCG,

Transposon E:
(SEQ ID NO: 5)
ACACCACACGGCCTAGAGTC,

Transposon F:
(SEQ ID NO: 6)
TGGACAATCACGCGACCAGC,

Transposon G:
(SEQ ID NO: 7)
TCATCTAACGCGCACCGTGC,

Transposon H:
(SEQ ID NO: 8)
TTCGTCGGCTCTCTCGAACC,

Transposon I:
(SEQ ID NO: 9)
TGGTGGAGCGTGCAGACTCT,

-continued

```
Transposon J:
                                    (SEQ ID NO: 10)
TATCTTCCTGCGCAGCGGAC, Transposon K:
                                    (SEQ ID NO: 11)
CTGACGTGTGAGGCGCTAGA, Transposon L:
                                    (SEQ ID NO: 12)
CCATCATCCAACCGGCTTCG, Transposon M:
                                    (SEQ ID NO: 13)
CACGAGAAGCCGTCCGCTTA, Transposon N:
                                    (SEQ ID NO: 14)
CGTACGTGCAACACTCCGCT, Transposon O:
                                    (SEQ ID NO: 15)
CTTGGTCAGGCGAGAAGCAC, Transposon P:
                                    (SEQ ID NO: 16)
GGCGTGATCAGTGCGTGGAT, Transposon Q:
                                    (SEQ ID NO: 17)
GAGCGTTTGGTGACCGCCAT, Transposon R:
                                    (SEQ ID NO: 18)
GCCTGCGGTCCATTGACCTA, Transposon S:
                                    (SEQ ID NO: 19)
GTAAGCCACTCCAGCGTCAC, Transposon T:
                                    (SEQ ID NO: 20)
GATCTGTTGCGCGTCTGGTG.
```

Using the above combination of transposon sequences for multiplex end tagging and amplification, single-cell DNA can be prepared into a sequencing library for next-generation sequencing. Shallow sequencing (with an average data amount of 8.3 Gb per cell) 6 single BJ cells on an Illumina sequencing platform achieved an average whole genome coverage of 56% (Table. 1). Deep sequencing (one HiSeq 4000 lane per cell) of 4 single BJ cells achieved an average coverage of 79%. Detection of SNVs is very accurate in these cells, with a false negative rate of 70% and a false positive rate of $8\times10^{-7}$/bp. Table 1 below shows the whole genome coverage of single cells amplified by multiplex end-tagging amplification (META) after shallow sequencing.

| Sample | Coverage (%) | Raw data Reads (M) | Bases (G) |
|---|---|---|---|
| PD10_XXL_SC20d10 | 48.75 | 53.648 | 8.101 |
| PD10_XXL_SC22d10 | 49.1 | 55.231 | 8.340 |
| PD10_XXL_SC24d10 | 54.24 | 40.486 | 6.113 |
| PD10_XXL_SC25d10 | 59.29 | 63.693 | 9.618 |
| PD10_XXL_SC26d10 | 65.32 | 67.716 | 10.225 |
| PD10_XXL_SC29d10 | 57.3 | 51.564 | 7.786 |

Example VIII

Methods of Mis-Priming for De Facto Multiplexing

Despite careful choice of a combination of transposon sequences, it is not uncommon for systematic insertion bias to still exist between transposons of different sequences. For example, for the combination of 20 sequences in Example VII, bias was observed in certain single-cell data, and frequencies of the most and least abundant sequences could differ by up to 10-fold, leading to a loss rate of more than the theoretical prediction of $\frac{1}{20}$, even though the rate is already less than 50%.

Figure 6:
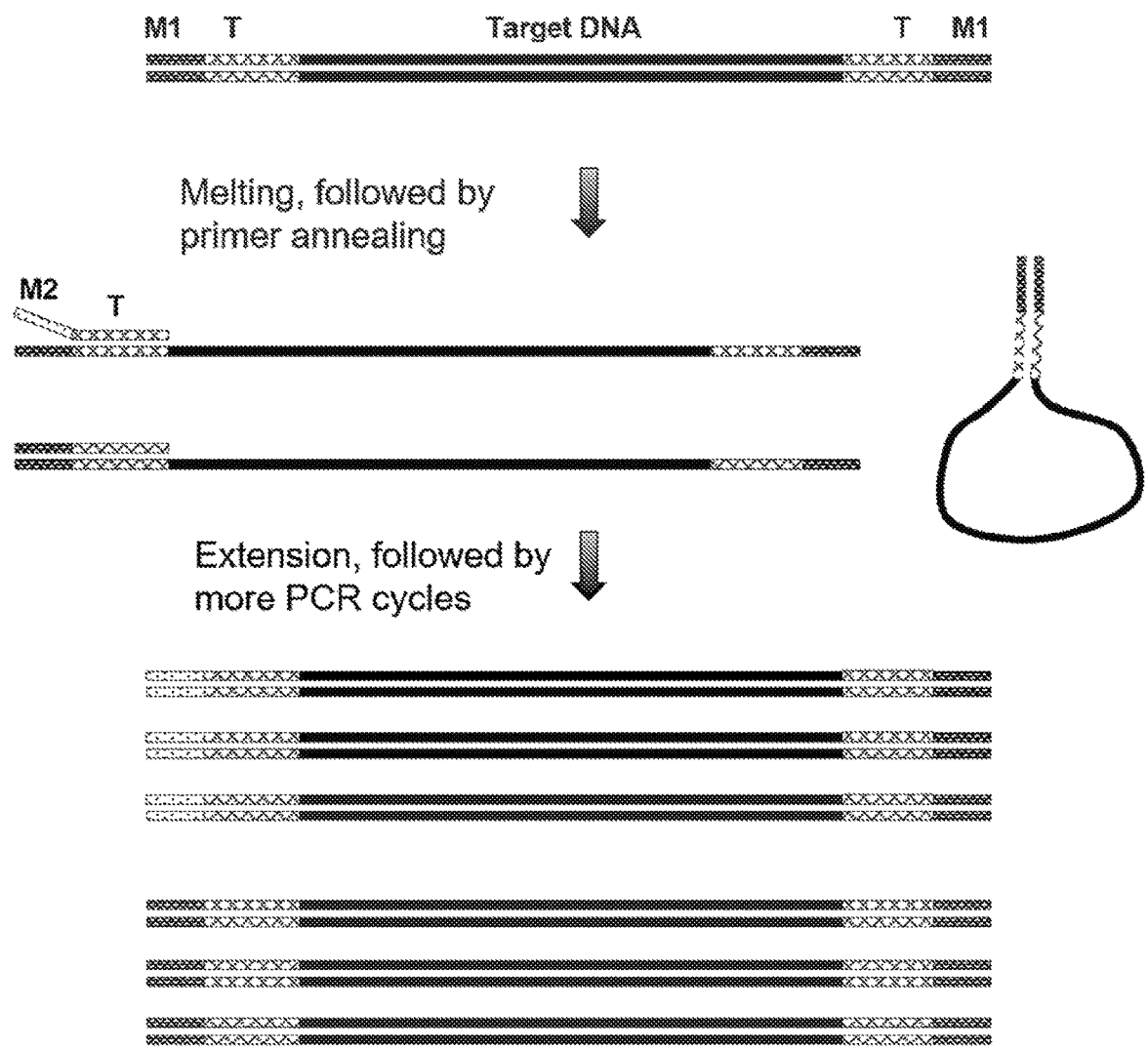
FIG. 6 depicts a method of de facto multiplexing via mis-priming.

Methods are provided for "mis-priming" to achieve de facto multiplexing. As shown in FIG. 6, a tagged DNA fragment with the same sequence on both ends could be primed by a primer with a different sequence after melting, resulting in a new fragment with different sequences on both ends after extension. This annealing of the partially specific primer ("mis-priming") is typically unlikely (hence the 50% loss in previous methods), because annealing of the fully specific primer ("proper-priming") is more favorable than that of the partially specific primer. However, when each M site is designed to be short compared to the T site, mis-priming may compete favorably with proper priming as well as self-looping. Note that when N is larger than two, there will be more partially specific primers than fully specific primers (assuming that the same concentration of each primer is added to the reaction mixture), helping to increase the chance of mis-priming and achieve de facto multiplexing.

Moreover, one can add a universal sequence to the T site, so that the M site becomes relatively short compared to T, which may help with mis-priming. To further increase the kinetic favorability of mis-priming, one can also increase the insertion length (e.g. by adding less concentrated transposome mixture), so that the fragments become longer on average, and that self-looping becomes less likely to compete with mis-priming.

Those of skill in the art can thus tune the concentration of primers, the length of M sites, length of the universal T site, and the insertion length to arrive at a balance between mis-priming and proper priming for de facto multiplexing, thereby minimizing loss of DNA.

Example IX

Filtering Out Amplification Artifacts for Variant Detection by Sequencing and Aligning Insertion Sites In addition to minimizing false negatives, multiplex end-tagging amplification of nucleic acids also offers an advantage of minimizing false positive detection of genetic variations. Recently, false positive detection has been reduced by Chen et al. and Dong et al., but hundreds or thousands of SNVs remain (Chen, C., Xing, D., Tan, L., Li, H., Zhou, G., Huang. L., & Xie, X. S. (2017). Single-cell whole-genome analyses by Linear Amplification via Transposon Insertion (LIANTI). Science, 356(6334), 189-194; Dong, X., Zhang, L., Milholland, B., Lee, M., Maslov, A. Y., Wang, T., & Vijg, J. (2017). Accurate identification of single-nucleotide variants in whole-genome-amplified single cells. Nature Methods). To further reduce false positives to nearly zero, a method of variant detection is provided.

Figure 7:
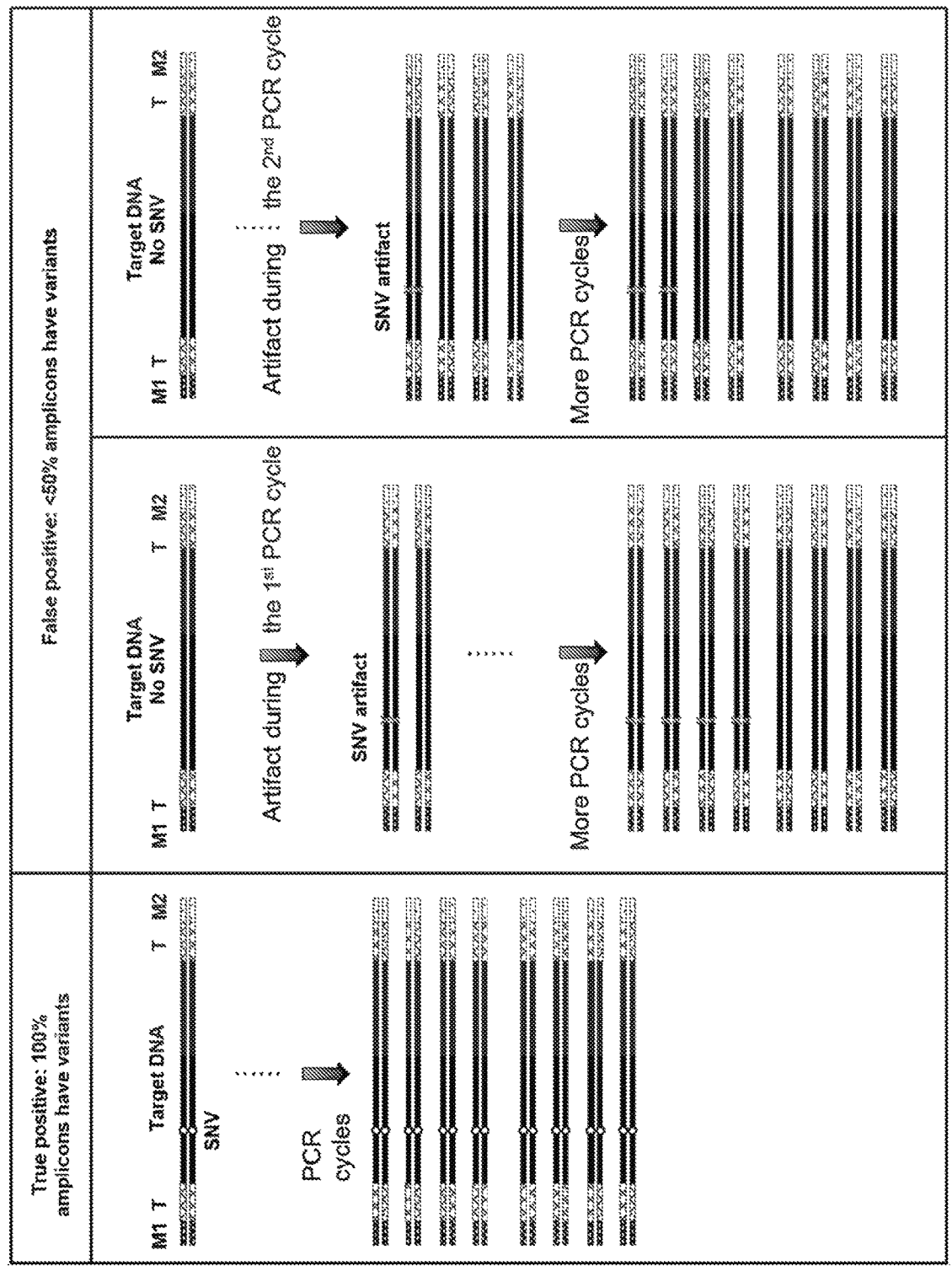
FIG. 7 is a schematic showing the distinction between true and false positives of single nucleotide variations (SNVs).

FIG. 7 shows how multiplex end-tagging amplification of nucleic acids allows for the identification of SNV false positives. After sequencing the amplified DNA using multiplex end-tagging amplification, reads that are aligned to the same genomic region and share the same M sequences ("barcodes") on both ends are grouped together. (In the example of FIG. 7, the M sequences are denoted as M1 and M2.) Within the same group of reads, if SNV is detected in 50% or less of the reads, it should be an artifact and be filtered out, because a true SNV positive will be present in 100%° of the reads in principle. The multiplex end-tagging amplification method described herein ensures that each amplified molecule contains barcodes, i.e. different and/or unique primer binding site sequences on both ends, so that both barcode matching and alignment to the reference genome can be used to group sequencing reads together.

A similar scheme can be used to identify structural variation (SV) false positives. Here, grouping of sequencing reads can be based only on one barcode and the target DNA sequence adjacent to the T site next to the barcode, rather than on barcodes of both ends and corresponding DNA sequences. This way, if a chimera artifact happens during PCR. 50% or less of the reads in the group will share with other reads only one barcode, rather than two, and share the DNA sequence adjacent to the T site next to the shared barcode. On the other hand, when there is a true positive of SV, the original DNA fragment bearing the true positive will be amplified into a group of molecules that all share the same barcodes on both ends and the same DNA sequence adjacent to the T site next to each barcode. So when sequencing reads are grouped only based on one barcode and the nearby target DNA sequence as mentioned above, true and false chimera positives can be distinguished. As a result, multiplex end-tagging amplification not only reduces false negatives by minimizing loss, but also allows for elimination of false positives for accurate detection of genetic variations.

Example X

Separate Analysis of Both Strands of DNA Molecules for Accurate Variant Detection Accurate detection of genomic variants in a single cell is crucial for early cancer diagnosis and preimplantation genetic screening. However, existing whole-genome amplification (WGA) methods produce many false positives (FPs). For example, cytosine and adenine deamination during cell lysis and DNA polymerase errors during WGA create FP single-nucleotide variations (SNVs), while chimera formation during WGA creates FP structural variations (SVs). Recent studies reduced FPs by linear amplification (Chen, C., Xing, D., Tan, L., Li, H., Zhou, G., Huang. L., & Xie, X. S. (2017). Single-cell whole-genome analyses by Linear Amplification via Transposon Insertion (LIANTI). Science, 356(6334), 189-194) or mild lysis conditions (Dong. X., Zhang. L., Milholland, B., Lee, M., Maslov, A. Y., Wang, T., & Vijg, J. (2017). Accurate identification of single-nucleotide variants in whole-genome-amplified single cells. Nature Methods); but hundreds or thousands of FPs remain. Sequencing kindred cells (Zong, C., Lu, S., Chapman, A. R., & Xie. X. S. (2012). Genome-wide detection of single-nucleotide and copy-number variations of a single human cell. Science, 338(6114), 1622-1626) can further reduce FPs; but kindred cells cannot be obtained when cells of interest cannot divide in vitro, for example in the case of human brain neurons (Lodato, M. A., Woodworth, M. B., Lee. S., Evrony. G. D., Mehta, B. K., Karger, A., . . . & Luquette, L. J. (2015). Somatic mutation in single human neurons tracks developmental and transcriptional history. Science. 350(6256), 94-98). In methods described herein, these FPs can be eliminated by separately analyzing the two strands of each DNA molecule, and requiring each variant to be observed from both strands. Because FPs are unlikely to occur at the same location and with the same pattern on both strands (for example, an FP SNV of cytosine deamination corresponds to a guanine on the complementary strand, which is not prone to deamination), methods of separately analyzing the two strands of each DNA molecule separately will lead to nearly zero FPs.

According to one aspect, the two strands of a double stranded DNA molecule can be physically or virtually separated from each other, and each variant is to be observed from both strands. Because FPs are unlikely to occur at the same location and with the same pattern on both strands (for example, an FP SNV of cytosine deamination corresponds to a guanine on the complementary strand, which is not prone to deamination), the present method of separately amplifying each strand of a double stranded DNA molecule, leads to nearly zero FPs. According to one aspect, any whole genome sequencing method can be used as long as the two strands can be separately amplified and sequenced. Particular examples include splitting a META reaction. i.e. multiplex end-tagging amplification, after the first cycle of PCR by pipetting into multiple tubes, virtually separating the two strands by multiple steps of PCR, or splitting an MDA reaction after alkaline denaturation into multiple tubes. In terms of sensitivity, assuming that a sample is physically split into N compartments with equal volumes, and that the WGA method has a loss probability of P for each strand, the theoretical false negative rate is $1-(1-P)^2(1-N^{-1})$, which is caused by (1) two strands going to a same compartment and/or (2) loss of either strand.

Figure 8:
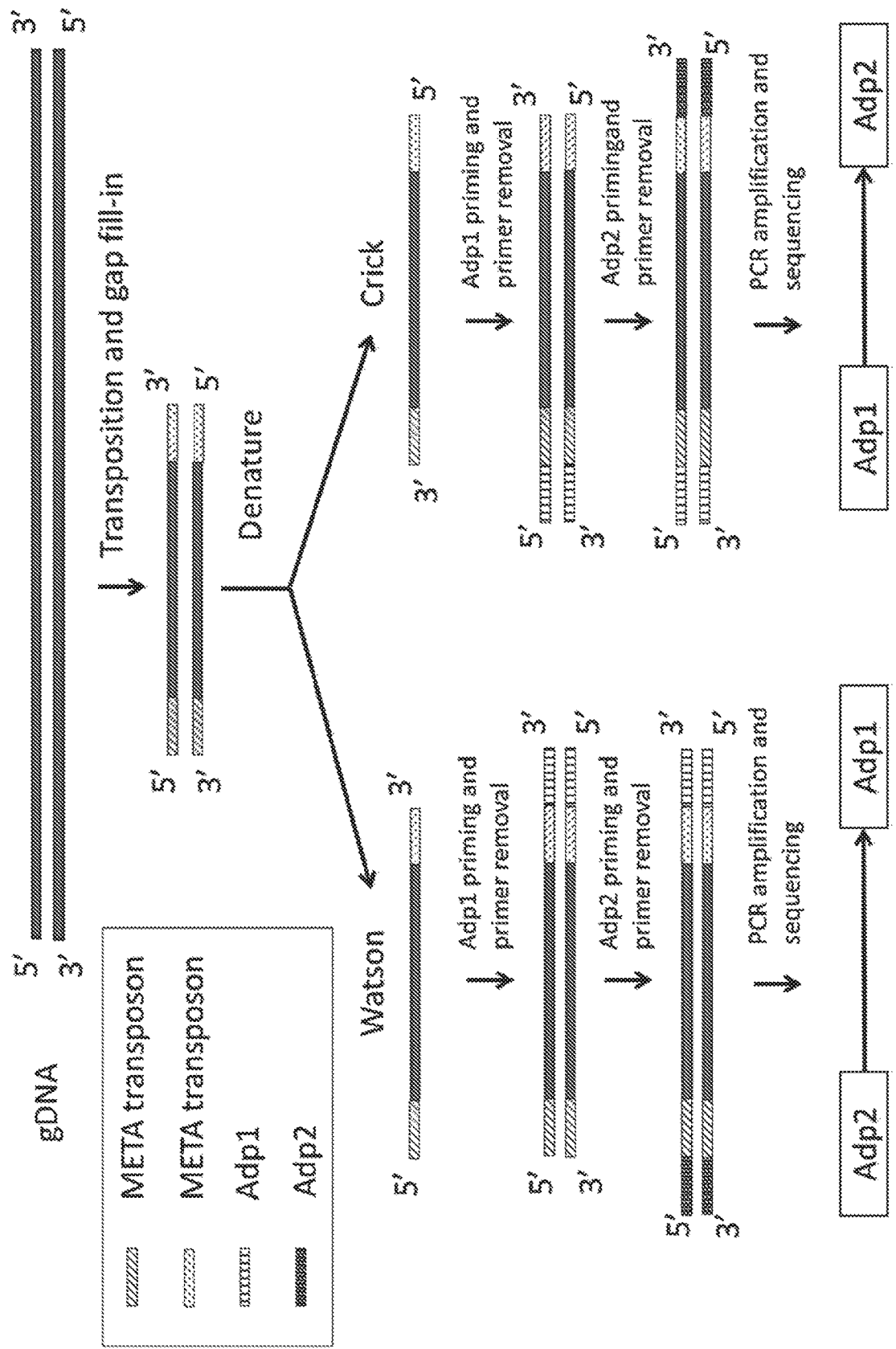
FIG. 8 is a schematic showing separate analysis of the two DNA strands (Watson and Crick) in a multiplex end-tagging amplification method as described herein.

For this application, PCR amplification of the multiplex end-tagging amplification protocol described herein will be separated into 3 stages (see FIG. 8). Each of the first two stages contain only one set of META PCR primers—with the Adp1 primer in the first stage, and the Adp2 primer in the second stage—and a single PCR cycle. The Adp1 and Adp2 primers contain two parts, one is the Adp1 or Adp2 sequence, the other one is a priming region that can prime to the priming site sequences of the META transposon DNA. The third stage contains two primers targeting both adaptors (for example, standard Illumina PCR primers). In this way, the final sequence obtained from an Illumina sequencer will retain strand information of the original DNA molecule, which can be used for accurate variant detection. According to one aspect, the Adp1 and Adp2 sequence can be part of Illumina's sequencing library adapter sequences.

Example XI

Sensitive Chromatin Conformation Capture Using Multiplex End-Tagging Amplification (META-C, Also Known as Dip-C for Diploid Cells) and its Accompanying Algorithm for Haplotype Imputation Methods described herein are directed to sensitive chromatin conformation capture using multiplex end tagging amplification (META-C), and when applied to a diploid cell, diploid chromatin conformation capture (Dip-C) and its accompany algorithm for haplotype imputation. When the input material is the product of chromatin conformation capture (3C) (Dekker, J., Rippe, K., Dekker, M., & Kleckner, N. (2002). Capturing chromosome conformation, science, 295(5558), 1306-1311) or related assays such as Hi-C (Lieberman-Aiden, E., Van Berkum, N. L., Williams, L., Imakaev, M., Ragoczy, T., Telling, A., . . . & Sandstrom. R. (2009). Comprehensive mapping of long-range interactions reveals folding principles of the human genome, science, 326(5950). 289-293), multiplex end-tagging amplification methods (META) described herein can detect the conformation of chromatin in single cells or small amount of materials. This modification of META, called META-C, detected $7 \times 10^5$ to $2 \times 10^6$ chromatin contacts per cell in 9 single GM12878 cells, more sensitive than existing methods (Nagano, T., Lubling, Y., Stevens, T. J., Schoenfelder, S., Yaffe, E., Dean, W., . . . & Fraser. P. (2013). Single-cell Hi-C reveals cell-to-cell variability in chromosome structure. Nature, 502(7469), 59-64; Nagano. T., Lubling, Y., Varnai, C., Dudley, C., Leung, W., Baran, Y., . . . & Tanay. A. (2016). Cell cycle dynamics of chromosomal organisation at single-cell resolution, bioRxiv, 094466; Stevens, T. J., Lando, D., Basu, S., Atkinson, L. P., Cao, Y., Lee. S. F., . . . & Cramard. J. (2017). 3D structures of individual mammalian genomes studied by single-cell Hi-C. Nature. 544(7648), 59-64; Flyamer, I. M., Gassler, J., Imakaev, M., Brandão, H. B., Ulianov, S. V., Abdennur, N., . . . & Tachibana-Konwalski, K. (2017). Single-nucleus Hi-C reveals unique chromatin reorganization at xocyte-to-zygote transition. Nature, 544 (7648), 110-114).

Most functional cells are diploid. When applied to diploid cells, the methods described herein utilize the statistical properties of chromatin contacts to impute the haplotype information of each contact. For each contact, an algorithm is provided that uses haplotypes of nearby contacts to determine its haplotypes. For example, for a contact joining position x (in base pairs) on one chromosome and position y on another, all contacts joining x' and y' of the same chromosome pair such that $(|x'-x|^{0.5}+|y'-y|^{0.5})^2 \leq 10$ Mb may be used to determine its haplotypes. The algorithm (referred to as Dip-C algorithm) then iteratively generates draft 3D structures and uses these structures to further impute haplotypes. For example, for each contact, haplotypes are chosen so that the resulting 3D distance is the smallest. This algorithm was applied to the 9 GM12878 single cells, and imputed haplotypes for the majority of contacts, yielding 3D genome structures at a 20-kb resolution.

Example XII

Sensitive Detection of Open Chromatin Using Multiplex End Tagging Amplification (METATAC)

Methods described herein are directed to sensitive detection of open chromatin using multiplex end tagging and amplification (METATAC.) When the input material is native or fixed cell nuclei, as in ATAC-Seq (Buenrostro. J. D., Giresi, P. G., Zaba. L. C., Chang, H. Y., & Greenleaf, W. J. (2013). Transposition of native chromatin for fast and sensitive epigenomic profiling of open chromatin. DNA-binding proteins and nucleosome position. Nature methods, 10(12), 1213-1218), multiplex end tagging and amplification can detect open chromatin in single cells or small amount of materials. This modification of META, called METATAC, detected 6% to 33% of the total open-chromatin regions per cell in 18 single GM12878 cells, more sensitive than existing methods (Buenrostro, J. D., Wu, B., Litzenburger, U. M., Ruff, D., Gonzales, M. L., Snyder, M. P., . . . & Greenleaf. W. J. (2015). Single-cell chromatin accessibility reveals principles of regulatory variation. Nature, 523(7561), 486-490; Cusanovich, D. A., Daza. R., Adey, A., Pliner, H. A., Christiansen. L., Gunderson, K. L., . . . & Shendure. J. (2015). Multiplex single-cell profiling of chromatin accessibility by combinatorial cellular indexing. Science, 348(6237), 910-914).

Example XIII

Kits

The materials and reagents required for the disclosed amplification method may be assembled together in a kit. The kits of the present disclosure generally will include at least the transposome (consists of transposase enzyme and transposon DNA), nucleotides, and DNA polymerase necessary to carry out the claimed method along with primer sets as needed. In a preferred embodiment, the kit will also contain directions for amplifying DNA from DNA samples. Exemplary kits are those suitable for use in amplifying whole genomic DNA. In each case, the kits will preferably have distinct containers for each individual reagent, enzyme or reactant. Each agent will generally be suitably aliquoted in their respective containers. The container means of the kits will generally include at least one vial or test tube. Flasks, bottles, and other container means into which the reagents are placed and aliquoted are also possible. The individual containers of the kit will preferably be maintained in close confinement for commercial sale. Suitable larger containers may include injection or blow-molded plastic containers into which the desired vials are retained. Instructions are preferably provided with the kit.

Example XIV

Embodiments

The present disclosure describes a method of DNA amplification including contacting genomic DNA with a library of transposomes with each transposome of the library having two transposases and two transposon DNA, wherein each transposon DNA includes a transposase binding site and a primer binding site sequence, wherein the primer binding site sequence is different from the primer binding site of other members of the transposome library, wherein the library of transposomes bind to target locations along the genomic DNA and the transposase cleaves the genomic DNA into a plurality of double stranded genomic DNA fragments representing a genomic DNA fragment library, with each double stranded genomic DNA fragment includes a unique and different primer binding site sequence on each end of the genomic DNA fragment, filling a gap between the transposon DNA and the genomic DNA fragment to form a library of double stranded genomic DNA fragment extension products having unique and different primer binding site sequences at each end, and amplifying the double stranded genomic DNA fragment extension products to produce amplicons. According to one aspect, the method further includes sequencing the amplicons. According to one aspect, each transposome within the library of transposomes includes two different primer binding site sequences. According to one aspect, each transposome within the library of transposomes includes two identical primer binding site sequences on each transposon of the transposome, which are different from primer binding site sequences in other transposomes of the library of transposomes. According to one aspect, the genomic DNA is whole genomic DNA obtained from a single cell. According to one aspect, the transposase is Tn5 transposase, Mu transposase, Tn7 transposase or IS5 transposase. According to one aspect, the transposon DNA includes a double-stranded 19 bp Tnp binding site and an overhang, wherein the overhang includes a unique and different primer binding site sequence at the 5' end of the overhang. According to one aspect, bound transposases are removed from the double stranded fragments before gap filling and extending of the double stranded genomic DNA fragments. According to one aspect, the genomic DNA is from a prenatal cell. According to one aspect, the genomic DNA is from a cancer cell. According to one aspect, the genomic DNA is from a circulating tumor cell. According to one aspect, the genomic DNA is from a single prenatal cell. According to one aspect, the genomic DNA is from a single cancer cell. According to one aspect, the genomic DNA is from a single circulating tumor cell. According to one aspect, the genomic DNA is the product of chromatin conformation capture from a single cell or a small sample. According to one aspect, the genomic DNA is the native or fixed chromatin from a single cell or minute amount of samples. According to one aspect, the unique and/or different primer binding site sequence is a specific PCR primer binding site. According to one aspect, the library of transposomes includes 1 to 100 unique and/or different primer binding site sequences. According to one aspect, the library of transposomes includes 1 to 10 unique and/or different primer binding site sequences. According to one aspect, the library of transposomes includes 5 to 50 unique and/or different primer binding site sequences. According to one aspect, the library of transposomes includes 30 to 100 unique and/or different primer binding site sequences. According to one aspect, the library of transposomes includes 15 to 25 unique and/or different primer binding site sequences. According to one aspect, the library of transposomes includes 100 to 1,000 unique and/or different primer binding site sequences. According to one aspect, the library of transposomes includes 1,000 to 10,000 unique and/or different primer binding site sequences. According to one aspect, the library of transposomes includes 10,000 to 100,000 unique and/or different primer binding site sequences. According to one aspect, the different primer binding site sequences are orthogonal.

The present disclosure describes a method of creating double stranded DNA amplicons having unique and/or different priming site sequences at each end including separating a target double stranded DNA having transposase binding sequence and the same priming site sequence at each end into a first single strand and second strand, annealing to the first strand, a first primer having a first sequence complementary to the transposase binding site and a second sequence noncomplementary to the priming site sequence, annealing to the second strand, a second primer having a first sequence complementary to the transposase binding site and a second sequence complementary to the priming site sequence, extending the first primer along the first strand and extending the second primer along the second strand and amplifying the extension products to produce double stranded DNA amplicons having unique and/or different priming site sequences at each end.

The present disclosure provides a method of amplifying two strands of a double stranded nucleic acid sequence having different priming sites at each end including separating the double stranded nucleic acid sequence into a first strand and a second strand, amplifying the first strand in the absence of the second strand to create first strand amplicons, amplifying the second strand in the absence of the first strand to create second strand amplicons, sequencing the first strand amplicons, and sequencing the second strand amplicons. According to one aspect, the method further includes annealing the 3'-end of the first strand and second strand with primers containing a priming region which is complementary to the 3'-end of the first strand and the second strand and a first adapter sequence, synthesizing complementary strands by a DNA polymerase, removing the excess primers with an exonuclease, annealing the 3'-end of the synthesized, complementary strands of the first strand and the second strand with primers containing a priming region which is complementary to the 3'-end of the first strand and the second strand and a second adapter sequence, synthesizing complementary strands by a DNA polymerase, removing the excess primers with an exonuclease, amplifying the target sequences by PCR with primers which anneal to the first adapter sequence and second adapter sequence to create amplicons for the first strand and the second strand, sequencing the amplicons to distinguish the first strand from the second strand, wherein the first end of the first strand is tagged with the first adapter, the second end of the first strand is tagged with the second adapter, and wherein the first end of the second strand is tagged with the second adapter, the second end of the second strand is tagged with the first adapter. According to one aspect, chromatin conformation capture is from a diploid sample, and haplotype information of each captured chromatin contact is determined.

What is claimed is:

1. A method of DNA amplification comprising
contacting genomic DNA with a library of transposomes with each transposome of the library having two transposases and two transposon DNA, wherein each transposon DNA includes a transposase binding site and a primer binding site sequence, wherein the primer binding site sequence is different from the primer binding site of other members of the transposome library, and wherein each transposome within the library of transposomes includes two different primer binding site sequences, wherein the library of transposomes bind to target locations along the genomic DNA and the transposase cleaves the genomic DNA into a plurality of double stranded genomic DNA fragments representing a genomic DNA fragment library, with each double stranded genomic DNA fragment includes a unique and/or different primer binding site sequence on each end of the genomic DNA fragment, filling a gap between the transposon DNA and the genomic DNA fragment to form a library of double stranded genomic DNA fragment extension products having unique and/or different primer binding site sequences at each end, and amplifying the double stranded genomic DNA fragment extension products to produce amplicons.

2. The method of claim 1 further including sequencing the amplicons.

3. The method of claim 1 wherein the genomic DNA is whole genomic DNA obtained from a single cell.

4. The method of claim 1 wherein the transposase is Tn5 transposase, Mu transposase, Tn7 transposase or IS5 transposase.

5. The method of claim 1 wherein the transposon DNA includes a double-stranded 19 bp Tnp binding site and an overhang, wherein the overhang includes a unique and/or different primer binding site sequence at the 5' end of the overhang.

6. The method of claim 1 wherein bound transposases are removed from the double stranded fragments before gap filling and extending of the double stranded genomic DNA fragments.

7. The method of claim 1 wherein the genomic DNA is from a prenatal cell.

8. The method of claim 1 wherein the genomic DNA is from a cancer cell.

9. The method of claim 1 wherein the genomic DNA is from a circulating tumor cell.

10. The method of claim 1 wherein the genomic DNA is from a single prenatal cell.

11. The method of claim 1 wherein the genomic DNA is from a single cancer cell.

12. The method of claim 1 wherein the genomic DNA is from a single circulating tumor cell.

13. The method of claim 1 where the genomic DNA is the product of chromatin conformation capture from a single cell or a small sample.

14. The method of claim 1 where the genomic DNA is the native or fixed chromatin from a single cell or minute amount of samples.

15. The method of claim 1 wherein the unique and different primer binding site sequence is a specific PCR primer binding site.

16. The method of claim 1 wherein the library of transposomes includes 1 to 100 unique and different primer binding site sequences.

17. The method of claim 1 wherein the library of transposomes includes 1 to 10 unique and different primer binding site sequences.

18. The method of claim 1 wherein the library of transposomes includes 5 to 50 unique and different primer binding site sequences.

19. The method of claim 1 wherein the library of transposomes includes 30 to 100 unique and different primer binding site sequences.

20. The method of claim 1 wherein the library of transposomes includes 15 to 25 unique and different primer binding site sequences.

21. The method of claim 1 wherein the library of transposomes includes 100 to 1,000 unique and different primer binding site sequences.

22. The method of claim 1 wherein the library of transposomes includes 1,000 to 10,000 unique and different primer binding site sequences.

23. The method of claim 1 wherein the library of transposomes includes 10,000 to 100,000 unique and different primer binding site sequences.

24. The method of claim 1 wherein the different primer binding site sequences are orthogonal.

* * * * *

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agaagccgtg tgccggtcta                                                 20

<210> SEQ ID NO 2
<211> LENGTH: 20
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 2
atcgtgcgga cgagacagca                                                  20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aatcctagca ccggttcgcc                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
acgtgttgca ggtgcactcg                                                  20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
acaccacacg gcctagagtc                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tggacaatca cgcgaccagc                                                  20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tcatctaacg cgcaccgtgc                                                  20

<210> SEQ ID NO 8
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 8
ttcgtcggct ctctcgaacc                                                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tggtggagcg tgcagactct                                                    20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tatcttcctg cgcagcggac                                                    20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctgacgtgtg aggcgctaga                                                    20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ccatcatcca accggcttcg                                                    20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cacgagaagc cgtccgctta                                                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 14
cgtacgtgca acactccgct                                           20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cttggtcagg cgagaagcac                                           20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggcgtgatca gtgcgtggat                                           20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gagcgtttgg tgaccgccat                                           20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gcctgcggtc cattgaccta                                           20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtaagccact ccagcgtcac                                           20

<210> SEQ ID NO 20
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 20
gatctgttgc gcgtctggtg                                                   20
```